US008608968B2

(12) United States Patent
Bryant et al.

(10) Patent No.: US 8,608,968 B2
(45) Date of Patent: Dec. 17, 2013

(54) COMPOSITIONS FOR BIOREMEDIATION AND METHODS FOR USING

(75) Inventors: James Daniel Bryant, Noblesville, IN (US); Keith Meyer, Wichita, KS (US)

(73) Assignee: Carus Corporation, Peru, IL (US)

( * ) Notice: Subject to any disclaimer, the term of this patent is extended or adjusted under 35 U.S.C. 154(b) by 1278 days.

(21) Appl. No.: 11/761,190

(22) Filed: Jun. 11, 2007

(65) Prior Publication Data

US 2008/0042101 A1    Feb. 21, 2008

Related U.S. Application Data

(60) Provisional application No. 60/812,785, filed on Jun. 12, 2006, provisional application No. 60/916,435, filed on May 7, 2007.

(51) Int. Cl.
*C02F 1/00* (2006.01)

(52) U.S. Cl.
USPC ............ 210/747.8; 210/747.7; 210/610; 405/128.15; 405/128.5; 554/1; 435/41; 435/262.5

(58) Field of Classification Search
USPC ............................................. 435/41; 252/175
See application file for complete search history.

(56) References Cited

U.S. PATENT DOCUMENTS

| | | | | |
|---|---|---|---|---|
| 5,514,588 | A * | 5/1996 | Varadaraj et al. | 435/262 |
| 5,561,059 | A * | 10/1996 | Kaiser et al. | 435/101 |
| 5,795,969 | A * | 8/1998 | Fehr et al. | 554/9 |
| 6,280,533 | B1 | 8/2001 | Hoppe et al. | |
| 6,398,960 | B1 | 6/2002 | Borden et al. | |
| 6,420,594 | B1 | 7/2002 | Farone et al. | |
| 6,527,970 | B1 * | 3/2003 | Scogin et al. | 252/3 |
| 6,806,078 | B2 | 10/2004 | Newman | |
| 2002/0166813 | A1 * | 11/2002 | Bartlett | 210/610 |
| 2004/0157317 | A1 | 8/2004 | Sorenson, Jr. et al. | |
| 2004/0220295 | A1 * | 11/2004 | Timcik et al. | 523/102 |

FOREIGN PATENT DOCUMENTS

| | | |
|---|---|---|
| CA | 2 426 216 | 10/2003 |
| EP | 1422001 A1 * | 5/2004 |
| WO | 2002/036498 | 10/2000 |
| WO | WO 0174984 A1 * | 10/2001 |

OTHER PUBLICATIONS

Coulibaly, KM et al. Impact of edible oil injection on the permeability of aquifer sands. Journal of Contaminant Hydrology. 2004. 71: 219-237.*
Fennell, DE et al. Dehalococcoides ethenogenes strain 195 reductively dechlorinates diverse chlorinated aromatic pollutants. Environ. Sci. Technol. 2004. 38: 2075-2081.*
Foglia, TA et al. Determination of biodiesel and triacylglycerols in diesel fuel by LC. Chromatographia. Aug. 2005. 62(3/4): 115-119.*
DiRienzo, MA et al. Effect of substitution of high stearic low linolenic acid soybean oil for hydrogenated soybean oil on fatty acid intake. Lipids. 2008. 43: 451-456.*
Gong, Z et al. Assessment of microbial respiratory activity of a manufactured gas plant soil after remediation using sunflower oil. Journal of Hazardous Materials. 2005. B124: 217-223. Available online on Jun. 27, 2005.*
Hunter, WJ. Bioremediation of chlorate or perchlorate contaminated water using permeable barriers containing vegetable oil. Current Microbiology. 2002. 45: 287-292.*
Sudar, R et al. Triacylglycerols composition of oil in OS soybean cultivars. Eur Food Res Technol. 2003. 217: 115-119.*
Lee et al. "New perspectives on microbial dehalogenation of chlorinated solvents: Insights from the field" Ann. Rev. Microbiol. 52:423-452 (1998).
Dybas et al. "Slow-release substrates for transformation of carbon tetrachloride by Pseudomonas strain KC" In Situ and On Site Bioremediation, vol. 3, Columbus, Battelle Press, p. 59 (1997).
Koenigsberg et al. "Time-release electron donor technology for accelerated biological reductive dechlorination" in: Wickramanayake, G.B., Gavaskar, A.R., Alleman, B.C., Magar, V.S. (Eds) Bioremediation and Phytoremediation of Chlorinated and Recalcitrant Compounds, Battelle Press. pp. 39-46 (2000).
Wu "A pilot study using HRC to enhance bioremediation of CAHs. Engineered approaches for In Situ Bioremediation of Chlorinated Solvent Contamination" Battelle Press, Columbus, Ohio, pp. 177-180 (1999).
Ludwig et al. "A permeable reactive barrier for treatment of heavy metals," Ground Water, 40(1): 59-66 (2002).
Waybrant et al. Treatment of mine drainage using permeable reactive barriers: Column experiments, Environ Sci Technol, 36(6): 1349-1356 (2002).
PCT International Search Report for PCT/US07/070889 completed by the U.S. Searching Authority (May 7, 2008).
Bryant, Dan, et al., "CAP18 Properties and Mechanisms, European Remediation Technologies", Aug. 2005, 15 pages.
Lee, M. D., et al., "Scale-Up Issues for In Situ Anaerobic Tetrachloroethene Bioremediation", Journal of Industrial Microbiology & Biotechnology, vol. 18, 1997, pp. 106-115.
Taylor, L. T., et al., "Bioremediation of Coal Tar PAH in Soils Using Biodiesel", Chemosphere, vol. 44, 2001, pp. 1131-1136.
Kusdiana, D., et al., "Kinetics of Transesterification in Rapeseed Oil to Biodiesel Fuel as Treated in Supercritical Methanol", Fuel, vol. 80, 2001, pp. 693-698.
European Search Report from related EP 07 863 357.5 dated Mar. 7, 2012, 3 pages.

* cited by examiner

*Primary Examiner* — Allison Ford
*Assistant Examiner* — Susan E Fernandez
(74) *Attorney, Agent, or Firm* — Clark Hill PLC

(57) ABSTRACT

Described herein are compounds, compositions, and methods useful for bioremediation of a contamination. In particular, described herein are compositions that include one or methyl esters of a fatty acid and one or more bioremediation reagents, and methods for their use.

30 Claims, 25 Drawing Sheets

COMPOSITIONS FOR BIOREMEDIATION AND METHODS FOR USING

CROSS REFERENCE TO RELATED APPLICATIONS

Reference is made to co-pending U.S. Provisional Application Ser. Nos. 60/812,785, titled "Additives for Bioremediation Oils and Methods for Using" filed Jun. 12, 2006, and Ser. No. 60/916,435, titled "Additives for Bioremediation Oils and Methods for Using" filed May 7, 2007, the disclosures of which are incorporated herein by reference in their entirety.

TECHNICAL FIELD

This invention pertains to compounds and compositions, and methods for using them to remediate environmental contamination including subsurface contamination. In particular, the compounds and compositions include one or more bioremediation reagents, fatty acid methyl esters, and derivatives thereof.

BACKGROUND

The world environment is encumbered with a number of sites that have been contaminated, often due to an existing or former manufacturing or production facility. These sites may be contaminated with any of a large number of organic compounds, metals and salts thereof, inorganic compounds, and others. Further, such sites may be located and isolated on the surface, or alternatively located underground. In the latter situation, the site may also be located near or within an underground water system, such as a ground water, an aquifer, or a vadose zone.

Although certain compounds and methods for decontaminating or remediating the contamination of such sites have been reported, other methods are yet needed. Current techniques may not be sufficient for sites that include particular mixture of contaminants, or for remediating sites more rapidly, or more thoroughly.

SUMMARY OF THE INVENTION

Described herein are compounds and compositions that are useful for decontaminating or otherwise remediating a contaminated site. In one embodiment, the compounds and compositions include a methyl ester of one or more fatty acids. Illustratively, the one or more fatty acids are derived from acyl glycerols, such as may be prepared from animal and vegetable sources. In one aspect, the one or more fatty acids are in about the same proportion as that found to naturally occur in the animal or vegetable oil. In another aspect, the one or more fatty acids are in about the same proportion as that found to naturally occur in the triglyceride fraction of the vegetable oil. Alternatively, the one or more fatty acids obtained from an vegetable or animal oil may be admixed with other methyl esters of fatty acids from a variety of other sources, including other animal and/or vegetable oil sources, either as individual components or predetermined mixtures, to prepare a different mixture or a different relative ratio of methyl esters in the resulting mixture of methyl esters of fatty acids. The one or more methyl esters of fatty acids described herein may be admixed with a wide variety of components used for the bioremediation of an organic, inorganic, or metal contamination, where the bioremediation includes sustaining or supporting the growth of a microbial population at the contamination site.

In another embodiment, the bioremediation reagent is an acyl glycerol, such as an animal or vegetable oil. In another embodiment, the bioremediation reagent is protamylasse. In another embodiment, the bioremediation reagent is in the form of an emulsion. In another embodiment, the bioremediation reagent is in the form of a flowable oil under ambient environmental conditions, including winter and summer climates.

In another embodiment, methods and apparatus are described for use with the compounds and compositions described herein to perform the decontamination or remediation of a contamination or contaminated site. In one aspect, the methods are used for a surface contamination. In another aspect, the methods are used for a subsurface contamination, such as for example a contamination located in a ground water, an aquifer, or a vadose zone.

The compounds, compositions, and methods described herein may be used to remediate a site contaminated with a wide variety of substances, including but not limited to organic compounds, such as halogenated organic compounds, nitrated organic compounds, sulfated organic compounds, and the like, inorganic compounds, such as nitrogen containing salts, sulfur containing salts, and the like, metals and salts thereof, including heavy metals, transition metals, and the like, and others.

DETAILED DESCRIPTION

Figure 1:
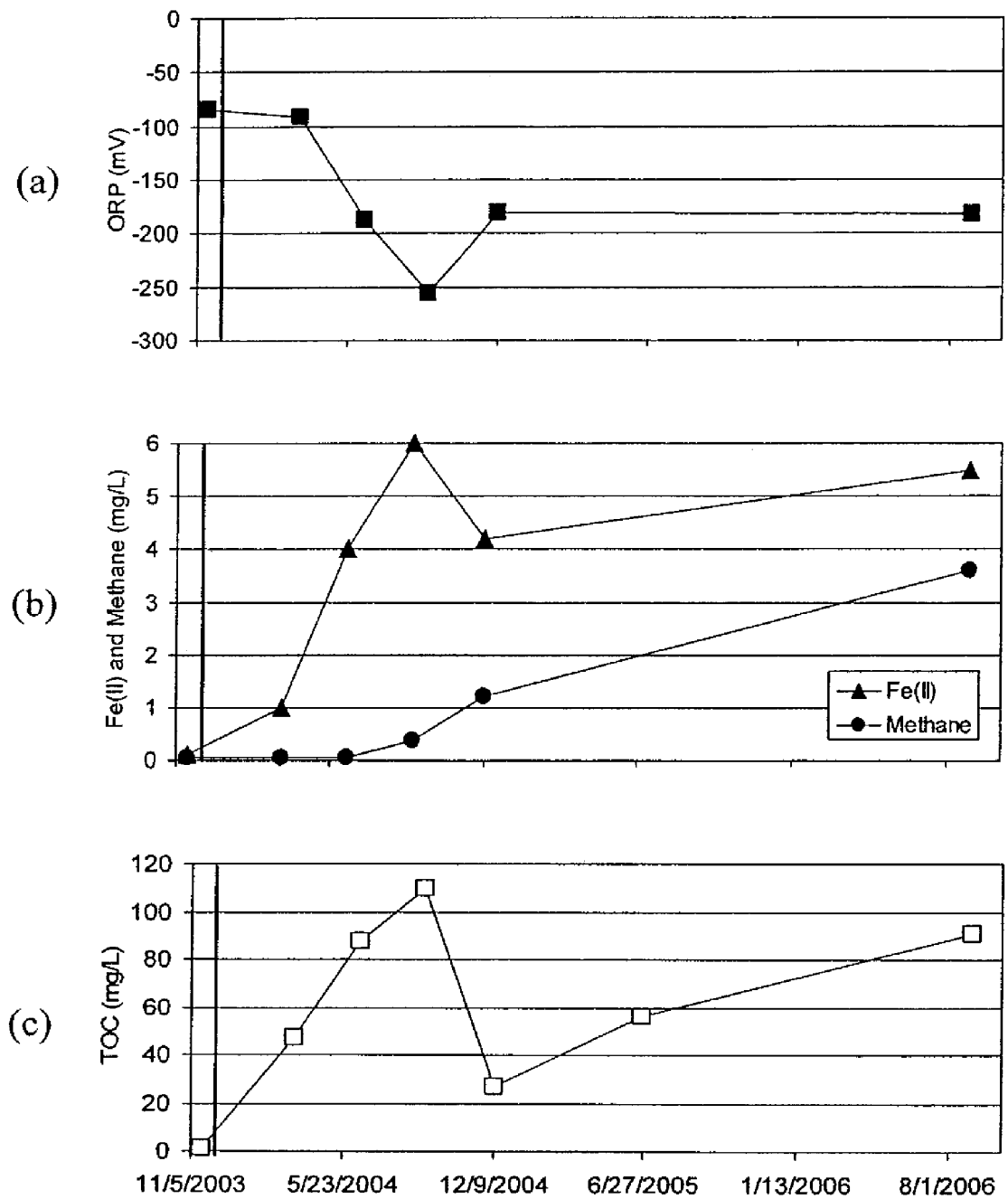
FIG. 1 show the effect on (a) Oxidation-Reduction Potential (ORP); (b) Iron II and methane production; and (c) Total organic carbon (TOC) content present in groundwater samples following treatment with CAP18 (indicated by the vertical line) as a function of time after the injection.

In one embodiment, the compounds and compositions described herein include one or more methyl esters of fatty acids admixed with one or more bioremediation reagents. As used herein, the term "fatty acid" refers to any long chain carboxylic acid, such as carboxylic acids having at least about 4 carbon atoms, such as butyric acid and crotonic acid, or at least about 8 carbon atoms, such as octanoic and/or octenoic acids. The fatty acids described herein may be saturated or unsaturated, including both cis and trans, or E and Z double bonds. The fatty acids described herein may be branched or unbranched. In an alternate embodiment, the fatty acids may include cyclized structures or fragments, such as 3-heptylcyclopentylheptanoic acid, 4-heptylcyclohexylheptanoic acid, and the like. The bioremediation reagent may be any of a wide variety of compounds or compositions, including any and all conventional bioremediation oils, that are used for the remediation or decontamination or mitigation of a contamination of a site, where a microbial population is either present and/or added, and used to anaerobically degrade, decompose or otherwise react with the contamination.

In another illustrative embodiment, the methyl esters of the fatty acids are prepared from one or more fatty acids in the range of about $C_{12}$ to about $C_{24}$ long chain carboxylic acids. In another illustrative embodiment, the methyl esters of the fatty acids are prepared from one or more fatty acids in the range of about $C_{14}$ to about $C_{22}$, or in the range from about $C_{16}$ to about $C_{22}$ long chain carboxylic acids. In another illustrative embodiment, the methyl esters of the fatty acids comprise primarily $C_{16}$ to $C_{18}$ long chain carboxylic acid esters. In another illustrative embodiment, the methyl esters of the fatty acids comprise primarily $C_{18}$ long chain carboxylic acid esters. It is to be understood that in any of these embodiments, the carboxylic acid fragments may be saturated and/or alternatively include one or more double or triple bonds. In another illustrative embodiment, the fatty acid esters comprise primarily $C_{18}$ long chain carboxylic acids, including one, two, or three double bonds. In another illustrative embodiment, the fatty acid esters comprise primarily unsaturated $C_{18}$ long chain carboxylic acids. In one variation, the methyl ester composition comprises at least about 50% $C_{18}$ fatty acids, or alternatively at least about 80% $C_{18}$ fatty acids.

It is appreciated that such ranges of carboxylic acids, including $C_{18}$ unsaturated fatty acids occur in varying amounts from natural sources, and each of these natural sources of fatty acids may be used to prepare the methyl esters thereof for use in the compositions and methods described herein.

In another illustrative embodiment, the methyl esters of fatty acids described herein include both saturated and unsaturated fatty acid fragments. In one aspect, the methyl ester composition comprises no more than about a 25% saturated fatty acids, or alternatively no more than about a 15% saturated fatty acids.

Such mixtures of fatty acid methyl esters described herein may also be characterized by average molecular weight and/or by average hydrogen yield under anaerobic conditions, such as those encountered during bioremediation of a contamination. In one aspect, the additives described herein have a weighted average molecular weight in the range from about 200 to about 350, in the range from about 250 to about 300, or in the range from about 270 to about 280. In another aspect, the additives described herein have a weighted average hydrogen yield in the range from about 10 to about 20, or in the range from about 12 to about 16.

In one illustrative embodiment, the methyl esters of fatty acids derived from or present in vegetable oils or fats are described and used in the compositions and methods. Such vegetable oils or fats, and derivatives thereof, include but are not limited to corn oils, canola oils, rapeseed oils, palm oils, olive oils, cottonseed oils, soybean oils, peanut oils, hydrolyzed or saponifed derivatives thereof, partially or fully hydrogenated variants thereof, cis/trans and/or E/Z isomers thereof, and mixtures thereof. In the case of such vegetable oils, it is appreciated that the fatty acids may be primarily components of acyl glycerides, and that the corresponding fatty acid esters may be prepared by hydrolysis and esterification, and/or by methanolysis.

In another illustrative embodiment, methyl esters of fatty acids derived or present in animal oils or fats are described. Such animal oils or fats, and derivatives thereof, include but are not limited to beef oils or fats, pork oils or fats, chicken oils or fats, buffalo oils or fats, hydrolyzed or saponifed derivatives thereof, partially or fully hydrogenated variants thereof, cis/trans and/or E/Z isomers thereof, and mixtures thereof. In the case of such animal oils, it is appreciated that the fatty acids may be primarily components of acyl glycerides, and that the corresponding fatty acid esters may be prepared by hydrolysis and esterification, and/or by methanolysis.

It is particularly appreciated that naturally occurring combinations of varying length carboxylic acids present in animal and vegetable oils and derivatives thereof provide convenient starting materials for preparing the methyl esters and compositions described herein. Such oils may include the fatty acids themselves, or various triglycerides of fatty acids. In either or both cases, the methyl ester additives described herein may be prepared from such fatty acids and/or triglycerides using conventional methods or alternatively as described herein.

Illustratively, the methyl esters are prepared from palm oils, which include C14:0 myristic (1.0%), C16:0 palmitic (44.3%), C18:0 stearic (4.6%), C18:1 oleic (38.7%), and C18:2 linoleic (10.5%) acids. Palm kernel oils include C8:0 caprylic (3.3%), C10 capric (3.4%), C12:0 lauric (48.2%), C14:0 myristic (16.2%), C16:0 palmitic (8.4%), C18:0 stearic (2.5%), C18:1 oleic (15.3%), and C18:2 linoleic (2.3%) acids, in approximately the indicated percentages.

Illustratively, the methyl esters are prepared from corn oils, which include about 59% polyunsaturated fatty acid, 24% monounsaturated fatty acid, and 13% saturated fatty acid.

Illustratively, the methyl esters are prepared from rapeseed and/or canola oils, which include about 40-50% C22:1 erucic acid, and the balance of other oils.

Illustratively, the methyl esters are prepared from soybean oils, which include triglycerides of C18:3 linolenic acid (11%); C18:2 linoleic acid (49%); and C18:1 oleic acid (26%), and saturated fatty acids (14%) in approximately the indicated percentages.

Illustratively, the methyl esters are prepared from olive oils, which include a high percentage of triglycerides of monounsaturated C18:1 oleic acid (55-80%).

Illustratively, the methyl esters are prepared from cottonseed oils, which include about 50% omega-6 fatty acid triglycerides, and others.

Illustratively, the methyl esters are prepared from sunflower oils, which include palmitic acid (4-9%), stearic acid (1-7%), oleic acid (14-40%), linoleic acid (48-74%), and others. It is appreciated that there are several types of sunflower oils that may be used in the compositions described herein, including high linoleic, high oleic and mid oleic sunflower oils. High linoleic sunflower oil generally has at least 69% linoleic acid. High oleic sunflower oil generally has at least 82% oleic acid. However, it is appreciated that variation in fatty acid profile is strongly influenced by both genetics and climate.

Other acids that may be included in the compounds and compositions described herein include, but are not limited to butyric, caproic, caprylic, capric, lauric, myristic, palmitic, stearic, arachidic, behenic, myristoleic, palmitoleic, oleic, linoleic, alpha-linolenic, arachidonic, eicosapentaenoic, erucic acid, and others.

In another illustrative embodiment, the oils used to prepare the fatty acid methyl esters are selected based on a predetermined ratio of saturated to unsaturated fatty acids, or alternatively on based on a predetermined ratio of monounsaturated to polyunsaturated acids, and other criteria. Illustratively, other natural sources of oils include varying relative amounts of saturated, monounsaturated, and polyunsaturated fatty acids. The following oils may be included in the compounds and compositions described herein, or alternatively, the compounds and compositions described herein may be derived from such oils, including but not limited to, coconut oil (85:7:2), palm oil (45:42:9), cottonseed oil (26:21:48), wheat germ oil (19:16:61), soya oil (15:23:57), olive oil (14:70:11), corn oil (13:25:58), sunflower oil (12:20:63), safflower oil (10:13:72), rapeseed oil (5:64:25), and others having the relative ratio of saturated, monounsaturated, and polyunsaturated fatty acids indicated.

It is to be understood that in each of the illustrative embodiments described herein, the percentages are approximate and naturally occurring variation is contemplated. Further, it is appreciated that different sources of such vegetable oils will naturally vary from the values described herein, which are intended to be exemplary of the invention described herein, but not construed in any way to be limiting. For example, ranges of linolenic acid in soybean oil may vary in the range from about 7% to about 12%. In addition, it is understood that in variations of the invention contemplated and described herein, such naturally occurring mixtures may be supplemented in various ways to increase the relative amount of one or more of a specific methyl ester present in the additive composition. For example, one source of oil may be selected for a particular ratio of chain length and then mixed with another source of oil selected for a particular ratio of saturation to unsaturation.

The one or more methyl esters of fatty acids described herein may be prepared by conventional methods including acid catalyzed esterification of carboxylic acids present in the oil source, initial hydrolysis and subsequent esterification, or alternatively by methanolysis. Alternatively, tri and diglycerides present in the oil source may be first hydrolyzed or saponified to free the acid, and after removal of glycerol, the acids are esterified. Alternatively, tri and diglycerides present in the oil source may be directly converted into methyl esters by reacting with any of a number of methoxide salts.

Bioremediation reagents suitable for admixing with the fatty acid methyl esters are also described herein. In one embodiment, the oils bioremediation reagents include acyl glycerols, such as those found in plant and animal sources. Such acyl glycerols may be mixtures of many components. Alternatively, such acyl glycerols may be relatively homogeneous and include a primary fraction of saturation level, and/or carbon chain length. For example, the oil may be primarily a saturated oil, or alternatively, the oil may be a primarily unsaturated oil, or more particularly a primarily monounsaturated or polyunsaturated oil. In another illustrative example, the oil may include a high percentage of a certain chain length or range of chain lengths as described herein. In each of these and other examples, the combination of the bioremediation oil and the one or more fatty acid methyl esters may be used for the in situ bioremediation of a contamination, where the compounds and compositions described herein are used by the microbial population as electron donors.

It is understood that any of the animal and/or vegetable oils described herein that may be used to prepare the one or more methyl esters of fatty acids, may also be used as the bioremediation reagent. Illustratively, the bioremediation reagent may be any animal oil or fat, such as but not limited to beef oils or fats, pork oils or fats, chicken oils or fats, buffalo oils or fats, partially hydrolyzed or saponifed derivatives thereof, partially or fully hydrogenated variants thereof, cis/trans and/or E/Z isomers thereof, and mixtures thereof. Illustratively, the bioremediation reagent may be any oils or fats, and derivatives thereof, include but are not limited to corn oils, canola oils, rapeseed oils, palm oils, olive oils, cottonseed oils, soybean oils, peanut oils, partially hydrolyzed or saponifed derivatives thereof, partially or fully hydrogenated variants thereof, cis/trans and/or E/Z isomers thereof, and mixtures thereof.

In another illustrative embodiment, the bioremediation reagent is a vegetable oil, and comprises triacyl glycerols of $C_{12}$ to $C_{24}$ long chain carboxylic acids. In another illustrative embodiment, the oil comprises triacyl glycerols of $C_{14}$ to $C_{22}$ or $C_{16}$ to $C_{22}$ long chain carboxylic acids. In another illustrative embodiment, the oil comprises triacyl glycerols primarily of $C_{16}$ to $C_{18}$ long chain carboxylic acids. In any of these embodiments, the triacyl glycerols may be saturated or alternatively include one or more double or triple bonds. In another illustrative embodiment, the triacyl glycerols comprise primarily $C_{18}$ long chain carboxylic acids, including one, two, or three double bonds. In one aspect, triacyl glycerols comprise primarily unsaturated $C_{18}$ long chain carboxylic acids. It is appreciated that such ranges of carboxylic acids, including $C_{18}$ unsaturated fatty acids occur in varying amounts from natural sources. In one variation, the bioremediation component comprises at least about 50% $C_{18}$ fatty acids, or alternatively at least about 80% $C_{18}$ fatty acids.

In another illustrative embodiment, the bioremediation reagent comprises triacyl glycerols of both saturated and unsaturated fatty acids. In one aspect, the bioremediation reagent comprises triacyl glycerols of no more than about a 25% saturated fatty acids, or alternatively no more than about a 15% saturated fatty acids.

It is to be understood that any of the methyl ester additives described herein may be admixed with any of the bioremediation compositions described herein, or with any other conventional or known bioremediation composition. In one embodiment, the bioremediation composition is prepared from a vegetable or animal oil, or a mixture thereof. In another embodiment, the bioremediation composition is prepared primarily or exclusively from a vegetable oil. In one variation, the bioremediation composition and the methyl ester additive are prepared from different animal and/or vegetable source oils. In another variation, the bioremediation composition and the methyl ester additive are prepared from the same animal and/or vegetable source oils. In another variation, the bioremediation composition and the methyl ester additive are each prepared primarily or exclusively from the same vegetable source oil or oils.

Illustratively, the methyl ester described herein are included in conventional bioremediation reagents. Bioremediation reagents that may be used in the compositions and methods described herein for remediation include, but are not limited to, vegetable oils, melted corn oil, coconut oil (see, Lee et al. "New perspectives on microbial dehalogenation of chlorinated solvents: Insights from the field" Ann. Rev. Microbiol. 52:423-452 (1998)), commercially available soybean emulsions, such as EOS (Edible Oil Substrate available from EOS Remediation, Inc, Raleigh, N.C., USA), edible oils, such as corn oil, hydrogenated cottonseed oil beads, solid food shortening (see, Dybas et al. "Slow-release substrates for transformation of carbon tetrachloride by Pseudomonas strain KC" In Situ and On Site Bioremediation, Vol. 3, Columbus, Battelle Press, p. 59 (1997)), protamylasse, mineral oils, animal oils, beef tallow, margarine, lactate, molasses, Hydrogen Release Compounds such as HRC, HRC-X, and the like, which are polymerized esters that dissolve over time and release lactate capable of supporting anaerobic biodegradation of other compounds, including chlorinated solvents, and other contaminants (see, Koenigsberg et al. "Time-release electron donor technology for accelerated biological reductive dechlorination" in: Wickramanayake, G. B., Gavaskar, A. R., Alleman, B. C., Magar, V. S. (Eds) Bioremediation and Phytoremediation of Chlorinated and Recalcitrant Compounds, Battelle Press. pp. 39-46 (2000); Wu "A pilot study using HRC to enhance bioremediation of CAHs. Engineered approaches for In Situ Bioremediation of Chlorinated Solvent Contamination" Battelle Press, Columbus, Ohio, pp 177-180 (1999)), and others.

It is understood that the bioremediation composition and the methyl esters described herein may be mixed in any relative proportion, including from about 1:99 to about 99:1. methyl ester to bioremediation composition. In another illustrative embodiment, the relative percentage of fatty acid methyl ester compared to the oil is less than 50%, and more particularly between about 1% and about 25%. In another illustrative embodiment, the relative percentage of methyl ester additives is between about 5% and about 25%, or between about 5% and about 15%.

It is appreciated that one potential limitation of certain bioremediation reagents that may be encountered is the competing production of methane by microorganisms during the bioremediation. Another limitation of certain bioremediation reagents that may be encountered is the competing reduction of carbon dioxide by microorganisms during the bioremediation. In each of these situations, the competing reduction increases the overall hydrogen demand of the bioremediation and may lead to the necessity of increasing the application amounts, and/or application rates, such as by augmentation, amendment, or supplementation during the treatment process to account for the loss of bioremediation composition to these competing processes. In addition, the production of methane and/or reduction of carbon dioxide may lengthen the overall decontamination time. It has been observed that $C_{18}$ carboxylic acids may inhibit methane production, sometimes termed methanogenesis, and/or decrease carbon dioxide reduction thereby improving the bioremediation treatment efficiency. It has also been observed that $C_{18}$ carboxylic acids may promote competition by for example dechlorinating microbial populations for hydrogen, relative to other hydrogen users, such as sulfate-reducers, and both mechanistic pathways of hydrogenotrophic methanogenesis and aceticlastic methanogenesis. It is appreciated that in particular both C18:1 and C18:2 unsaturated fatty acids may inhibit methanogenesis. Accordingly, in another illustrative embodiment, the additives described herein, as well as optionally the bioremediation oils, include a high percentage of $C_{18}$ fatty acid components, and more particularly C18:1 and C18:2 unsaturated fatty acid components.

The compounds, compositions, and methods described herein are useful with natural attenuation processes that may occur in situ and that are mediated by indigenous microbial populations present at contamination sites. In addition, the compounds, compositions and methods described herein are useful with enhanced anaerobic bioremediation conditions. Such enhanced conditions may be achieved by stimulating the indigenous microbial populations through the addition of electron donors. In addition, bioaugmentation may also be included in the methods described herein and be used in conjunction with the compounds and compositions described herein. As used herein, bioaugmentation includes processes in which a microbial population known to promote or complete reductive dechlorination is introduced into the contamination site, such as to groundwater, to enhance the rate and/or extent of biodegradation.

In another embodiment, the compounds and methods described herein are used with an already present or indigenous microbial population. In one variation, the indigenous population is supplemented with another population of the same or different microbial organisms. Illustrative microbial populations that are indigenous microbial populations may include representatives of the genera *Psuedomonus, Acinetobacter, Bacillus, Dehalobacter, Desulfobacterium*, and *Dehalococcoides*.

Illustrative microbial populations that may be added to introduce a microbial population or supplement an indigenous microbial population may include cultures of various strains of *Dehalococcoides*, including commercially-available cultures such as KB-1 DECHLORINATOR (KB-1, available from SiREM, Guelph, Ontario, Canada), Bio-Dechlor INOCULUM (available from Regenesis, San Clemente, Calif.), and the like. KB-1 is a natural microbial consortium containing microorganisms (*Dehalococcoides*). KB-1 has been reported to be non-pathogenic and is considered to be responsible for mediating the complete dechlorination of halocarbon contaminations, including TCE, cis-1,2-DCE, and VC to hydrocarbons such as ethene and/or ethane.

It is appreciated that many other components may also be included in the compositions described herein, including but not limited to other compounds or substances that are useable by the microbial population, including but not limited to molasses, liquid soybean oil, fully hydrogenated soybean wax, blown soybean oil, soy methyl ester, mineral oil, oleyl lactylic acid, oleic acid, lactic acid and salts and esters thereof, oleyl lactylic acid, linoleyl lactylic acid, linolenoyl lactylic acid, stearoyl lactylic acid, palmitoyl lactylic acid, myristoyl lactylic acid, lauroyl lactylic acid, caproyl lactylic acid, fatty acids and salts thereof, propylene glycol, glycerol, glutamate, mixtures of proteose peptone, beef extract, yeast extract, malt extract, dextrose, ascorbic acid, cellulose, chitin, and mixtures thereof.

In one illustrative formulation, the compounds and compositions described herein are free flowing oils under ambient conditions for introducing into contaminated sites. In another illustrative formulation, the compounds and compositions described herein are solid or semi-solid materials under ambient conditions, and which may be alternately heated to generate free flowing oils for introducing into contaminated sites. In another illustrative formulation, the compounds and compositions described herein are emulsified as an oil-in-water emulsion, such as may be prepared by high energy mixing. In one aspect, the emulsion includes small uniformly sized droplets, and one or more optional surfactants. In another aspect, both the compound or composition and the surfactant are useable by a microbial population, though it is appreciated that some components of the oil may be modified or degraded by other mechanisms in situ before the microbial population uses them. For example, triglycerides are generally degraded or hydrolyzed to the free fatty acid before the microbial population uses the fatty acid component as an energy source.

Any conventional bioremediation equipment capable of introducing the compounds and compositions into the contaminated site may be used to carry out the methods described herein. Illustrative techniques for introducing the compositions described herein include direct-push application methods and monitoring and injection well application methods, including but not limited to direct-push injection equipment, including Geoprobe tooling or Geoprobing, and/or monitoring wells, including permanent wells, temporary wells, piezometers, double diaphragm pumps, grout pumps, and the like. In addition, any application technique may be used with the compositions described herein, including both curtain and cascade design techniques. Cascade designs include the use of a grid pattern or injection points. Curtain designs include the application of a barrier through which ground water may move.

Illustratively, the bioremediation equipment capable of introducing the compounds and compositions into the contaminated site is a Geoprobe 6600-series direct push drilling machine, 1.5-inch diameter probe rods, equipped with a pressure-activated injection probe, and a GS-1000 grout pump. In addition, it is to be understood that other more conventional equipment may also be used with the methods and compositions described herein.

Any conventional bioremediation method that includes the step of introducing one or more of the compounds and/or compositions described herein may be used. Illustratively, the bioremediation method includes the steps where a Geoprobe is used to advance a hollow drill rod with a pressure-activated injection probe to a target depth. Upon reaching the target depth, a grout pump begins pumping the compounds and pressurizes the injection rods. The same opens one or more pressure-activated injection probes, and injects the compounds described herein, along with any optional additional components either simultaneously, contemporeously, or stepwise, into the subsurface formation. After injecting the intended amount, the drill rod is extracted an additional distance, such as for example about two to four feet, and an additional amount of the compounds and compositions are injected. This process is repeated throughout the full vertical extent of the intended treatment zone. A plurality of points can be utilized to address an entire contaminated area. Alternatively, one or more rows of injection points can be installed parallel to the direction a plume is migrating, in order to intersect and treat the plume as it migrates through the treatment area. In addition, it is to be understood that other more conventional equipment may also be used with the methods and compositions described herein.

In another embodiment, the remediation method includes a permeable reactive barrier (PRB). In a PRB process, a trench is excavated across a contaminant plume, such as an AMD plume, and backfilled with a compound or composition described herein. In one variation, a pH buffer, such as magnesium hydroxide, sodium bicarbonate, sodium hydroxide, limestone, and the like may be added. It is appreciated that the compound or composition included in such a method is an organic material and may therefore provide a carbon source to stimulate or sustain a microbial population capable of reducing certain contaminants like iron, sulfate, and the like. Without being bound by theory, it is suggested herein that the process may also result in a contemporaneous increase in the pH at the introduction site and effect immobilization of heavy or transition metals, such as chromium. See generally, Ludwig et al. 2002. "A permeable reactive barrier for treatment of heavy metals," Ground Water, 40(1):59-66 (2002); Waybrant et al. "Treatment of mine drainage using permeable reactive barriers: Column experiments," Environ Sci Technol, 36 (6): 1349-1356 (2002). Alternatively, it may be that the generally reducing environment results in the conversion of sulfate to sulfide, and accordingly, transition metals or heavy metal may form insoluble sulfide precipitates.

The compounds, compositions, and methods described herein may be used to remediate a contamination in a wide variety of sites, locations, or environments. In one illustrative configuration, the remediation site is a ground water, an aquifer, and/or a vadose zone.

The compounds, compositions, and methods described herein may be used to remediate a wide variety of contaminating substances. In one embodiment, the compounds, compositions, and methods described herein are used to remediate a site that is contaminated with one or more inorganic compounds, such as nitrite, nitrate, elemental sulfur, sulfites, sulfates, sulfur dioxide, pyrite ($FeS_2$), pyrrhotite (FeS), chalcopyrite ($CuFeS_2$), enargite ($Cu_3AsS_4$), perchlorate, nitro-containing compounds and explosives, such as RDX, MNX, DNX, TNX, HMX, TNT, DNT, aminotoluenes, and the like, collective wastes such as acid mine drainage, and the like.

In another embodiment, the compounds, compositions, and methods described herein are used to remediate a site that is contaminated with one or more organic compounds, including halogenated organic compounds, such as tetrachloroethylene, also referred to as perchloroethylene (PCE), trichloroethylene (TCE), drichloroethylene (DCE), including cis-DCE, 1,2-DCA, vinyl chloride (VC), trichloroethane (TCA), dichloroethane (DCA), chloroethane (CA), chloromethanes, and the like, halogenated aromatic compounds such as trichlorobenzene, dichlorobenzene, and the like, alcohols, ethers, such as MTBE, and the like, pesticides, herbicides, dyes, and mixtures thereof.

In another embodiment, the compounds, compositions, and methods described herein are used to remediate a site that is contaminated with chlorinated aliphatic compounds including tetrachloroethylene, also referred to as perchloroethylene (PCE), trichloroethylene (TCE), drichloroethylene (DCE), including cis-1,2-DCE, and vinyl chloride (VC). It is appreciated that one illustrative degradation pathway leading to decontamination of such sites includes the conversion of PCE to TCE, then to cis-1,2-DCE, then to VC, and finally to ethene and/or ethane. Other organic compounds may proceed through a similar pathway, and still others may undergo a more complex pathway in which there may be inorganic processes involved. For example, TCA can degrade biologically first to dichloroethane, then subsequently to chloroethane, then to ethane, and other products as described herein. Alternatively, TCA can degrade abioitically first to 1,1-dichloroethene which can then degrade under anaerobic conditions. Therefore, it is understood that site contamination that includes TCA may already include substantial amounts of 1,1-dichloroethene priot to the administration of introduction of any of the compositions described herein. Following introduction of such compositions, 1,1-dichloroethene can be degraded to vinyl chloride, then to ethane, and other products as described herein. It is appreciated that some steps in that overall conversion may proceed more slowly than others. For example, the step of converting PCE to TCE may be slower than the subsequent conversion of TCE to cis-1,2-DCE. Accordingly, in situ monitoring of the site may result in very low measurable concentrations of TCE relative to PCE and cis-1,2-DCE. Similarly, the conversion of cis-1,2-DCE to VC may be slower than the subsequent conversion of VC to ethene and/or ethane, such that measurable concentrations of VC may be low compared to those of ethene and/or ethane. Finally, it is understood that under certain conditions, ethene and/or ethane may be subsequently converted into methane. It is appreciated that this final step may not be necessary to effectively remediate a contamination. Further, that final step may consume the bioremediation components thus requiring an additional amount of bioremediation composition to be added to the site for complete decontamination. Accordingly, it is understood that bioremediation compositions that are less available for the conversion of ethene and/or ethane into methane, or moreover, inhibit the conversion of ethene and/or ethane into methane may be desirable or advantages in remediating certain contaminations that include chlorinated organic compounds.

In another embodiment, the compounds, compositions, and methods described herein are used to remediate a site that is contaminated with a relatively high concentration of one or more organic compounds, including the specific organic compound contaminants described herein. It is appreciated that additional ingredients may be included in the compositions or methods described herein. Illustratively, strong oxidizing agents may be used in the methods and also introduced or administered to the contamination. It is appreciated that certain strong oxidants are injected separately, typically at separate times to avoid reaction and/or destruction of the bioremdieation compositions described herein prior to administration or introduction to the contamination. An illustrative variation of the methods described herein that includes the step of administering oxidizing agents is to first inject the oxidant in a concentrated source area, wait for a predetermined period of time (for example, several weeks or even months), then inject the composition, such as CAP18 or CAP18-ME both in the source area as well as the larger plume area. Alternatively, the oxidants may be injected in the source area and then at the same time the compositions are injected, such as CAP18 or CAP18-ME in the plume area only. Illustrative oxidizing agents include, but are not limited to, permanganate, peroxides, and the like. For example, in one aspect, potassium, sodium, or other salts of permanganate may be admixed or coinjected with the compositions described herein. In another aspect, peroxides, including peroxides catalyzed by transitions metal salts, such as Fenton's reagent, may be admixed or coinjected with the compositions described herein.

In another embodiment, the compounds, compositions, and methods described herein are used to remediate a site that is contaminated with one or more metals, including transition metals, such as iron, aluminum, chromium, copper, zinc, manganese, cadmium, nickel, cobalt, and uranium.

In another embodiment, the bioremediation is accomplished with a microbial population by using the compounds and compositions described herein as electron donor sources, and correspondingly using the contaminant to be remediated as an electron acceptor, thereby reducing the electron acceptor to a compound exhibiting a lower negative or deleterious environment impact. Illustratively, the contaminant is an organic or non-aqueous halogenated compound, such as PCE, TCE, DCE, cis-DCE, 1,2-DCA, VC, TCA, DCA, CA, chloromethanes, and the like, and the microbial population reduces the contaminant by dehalogenation.

It is understood that certain anaerobic microbial populations use as a food source compounds or substances that would otherwise be considered as environment contaminants or environmental contamination. In one aspect, such microbial populations use those contaminants as electron acceptors, in combination with other compounds as electron donors in respiring metabolism. In so doing, the contaminants are reduced to compounds with a lower adverse environmental impact. However, in order for the metabolically directed redox reaction to take place, a sufficient supply of electron donor compounds or compositions must also be present to sustain the microbial population. In one aspect, the compounds and methods describe herein are for supplying the electron donor compounds needed by the microbial population. In another aspect, the compounds and methods described herein are for accelerating or enhancing the decontaminating ability of the microbial population.

In another illustrative embodiment, the compounds and compositions, and the methods for using the compounds and compositions described herein are adapted for a rapid onset of strongly anaerobic conditions. It is understood that depending upon the composition of the bioremediation composition, long half-lives of components may be balanced against a relatively slow onset of reducing conditions that will be sufficient to assess the progress of bioremediation. For example, as shown in FIG. 1, CAP18 shows long-term activity in the treatment site, thus precluding the necessity of a reapplication of bioremediation composition. FIGS. 1($a$) and 1($b$) show that reductive conversion continues after nearly three years following the initial application. However, the desirable strongly anaerobic conditions did not peak within the first 6 months after the application. The additives described herein may be included in compositions designed for rapid onset. In one aspect, the additives are included at the higher relative concentrations described herein to promote stronger reducing conditions at an earlier date following introduction or administration of the bioremediation composition. It is appreciated that such rapid onset formulations and methods will also promote the use of small and/or brief pilot tests to achieve remediation in a shorter timeframe than would otherwise be possible.

Additional details for determining the amount of bioremediation oil to be introduced into a contaminated site based on soil and ground water sampling are described at http://www.dbiproducts.com/, the information contained thereon is incorporated herein by reference.

EXAMPLES

General Methyl Ester Preparation

Combine 992 mL vegetable oil with 141 mL 1 N NaOH. 1.7 mL of 0.25 N NaOH or 0.425 mL of 1 N NaOH is used to neutralize 7.05 g (1.01 g/mL) of vegetable oil calculated to 1.7% free fatty acids present in oil. Excess base may be used as described herein to facilitate more complete removal of soaps and fatty acids. It is to be understood that in that context, an excess includes +1% or more. Alternatively, stoichiometric amounts may be used. Mix and allow soaps to settle out of solution. Decant soaps. Water wash oil with 100 mL distilled $H_2O$ too remove residual soaps, by adding distilled water to oil and mix. Allow water to settle out of solution. Decant the water. Add 200 mL of sodium methoxide solution (prepared from 200 mL methanol and 3.5 gm NaOH) to oil and mix with heat. Allow glycerol to settle out of solution. Decant the glycerol. Add 50 mL distilled $H_2O$ to solution and stir. Allow water to settle out and decant. Optionally, allow methyl esters to sit for an additional 1-2 weeks until liquid is transparent, which may result in a more complete removal of additional glycerols and water. Decant any residual material from bottom of container prior to use.

CAP18

Figure 2:
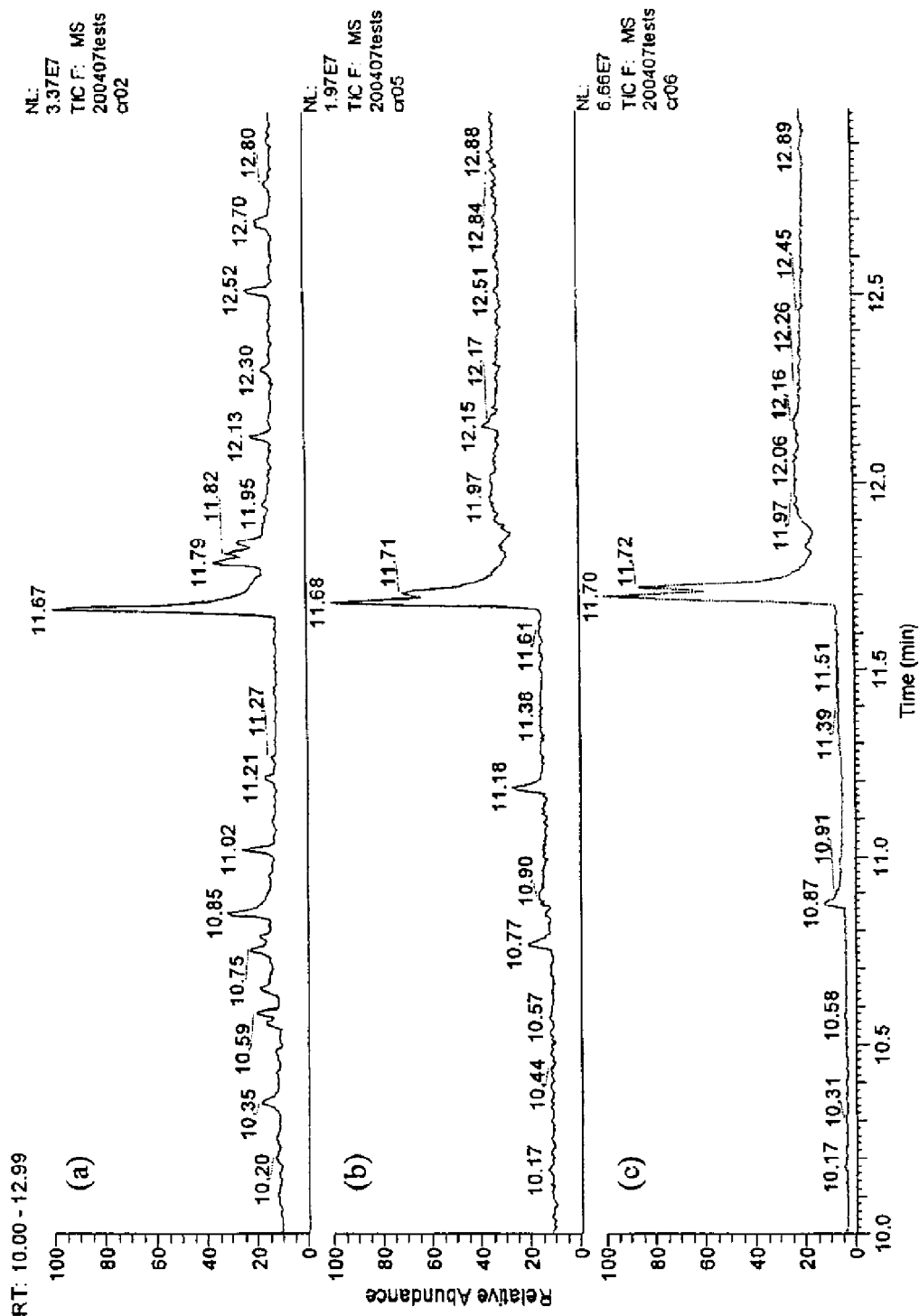
FIG. 2 shows the GC-MS spectra fatty acid samples from: (a) commercially available linoleic acid; (b) Protamylasse (AA 2726, melasse); (c) CAP18.

Material was obtained from DBI Remediation Products LLC (Fishers, Ind.). The GC-MS spectrum of the CAP18 is shown in FIG. 2(c), and compared to two other commercial sources of vegetable oil products, FIG. 2(a) neat linoleic acid, and FIG. 2(b) protamylasse. The retention times for linoleic acid are 11.67, 11.68, 11.70 min; the retention times for oleic acid are 11.71, 11.72 min.

Methyl Esters Derived from CAP18

Figure 3:
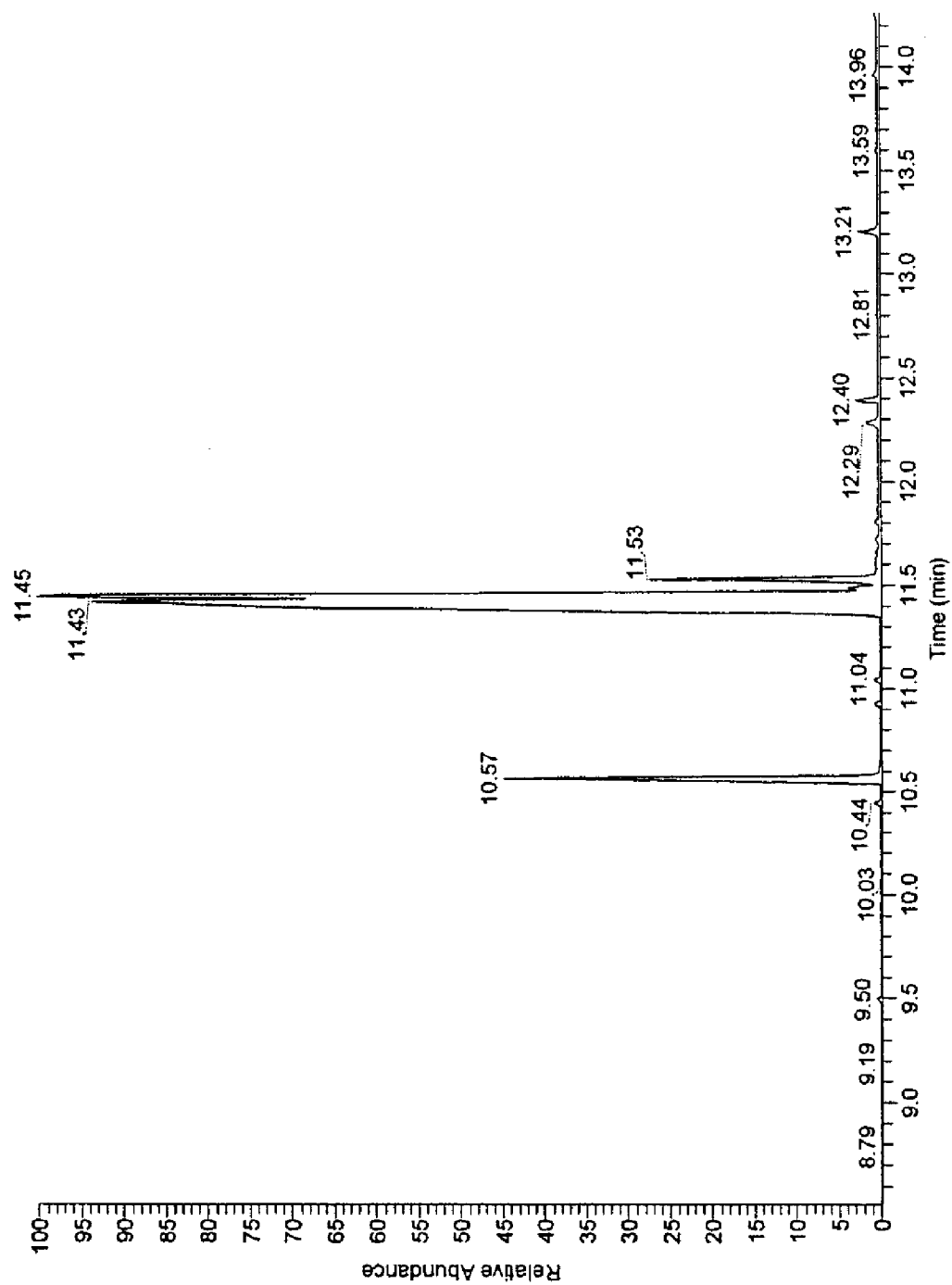
FIG. 3 shows a GC-MS of a mixture of methyl esters prepared from CAP18.
Figure 4:
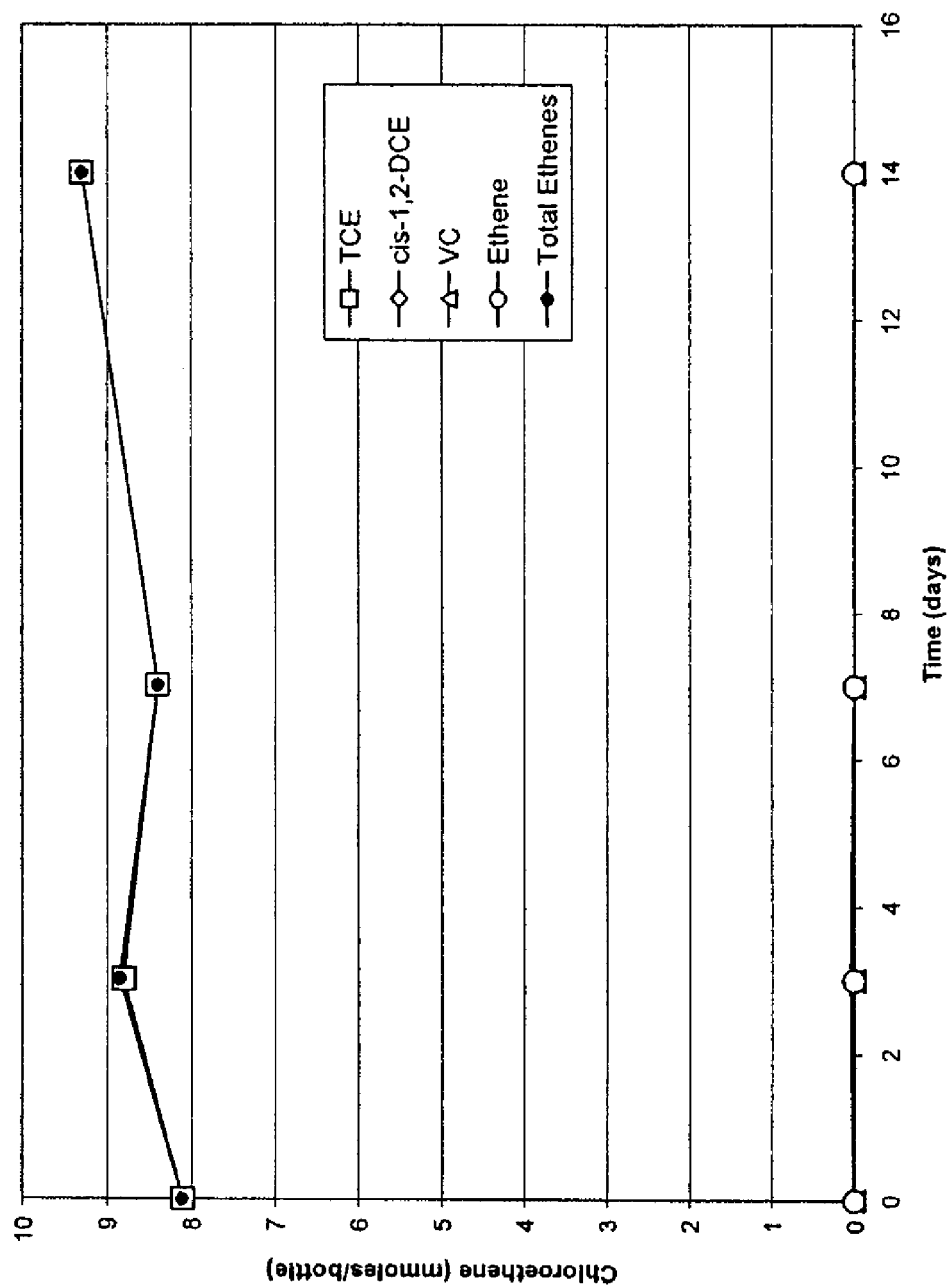
FIG. 4 shows the full analysis of the degradation of trichloroethene (TCE) by CAP18 as a control (Sample 1).
Figure 5:
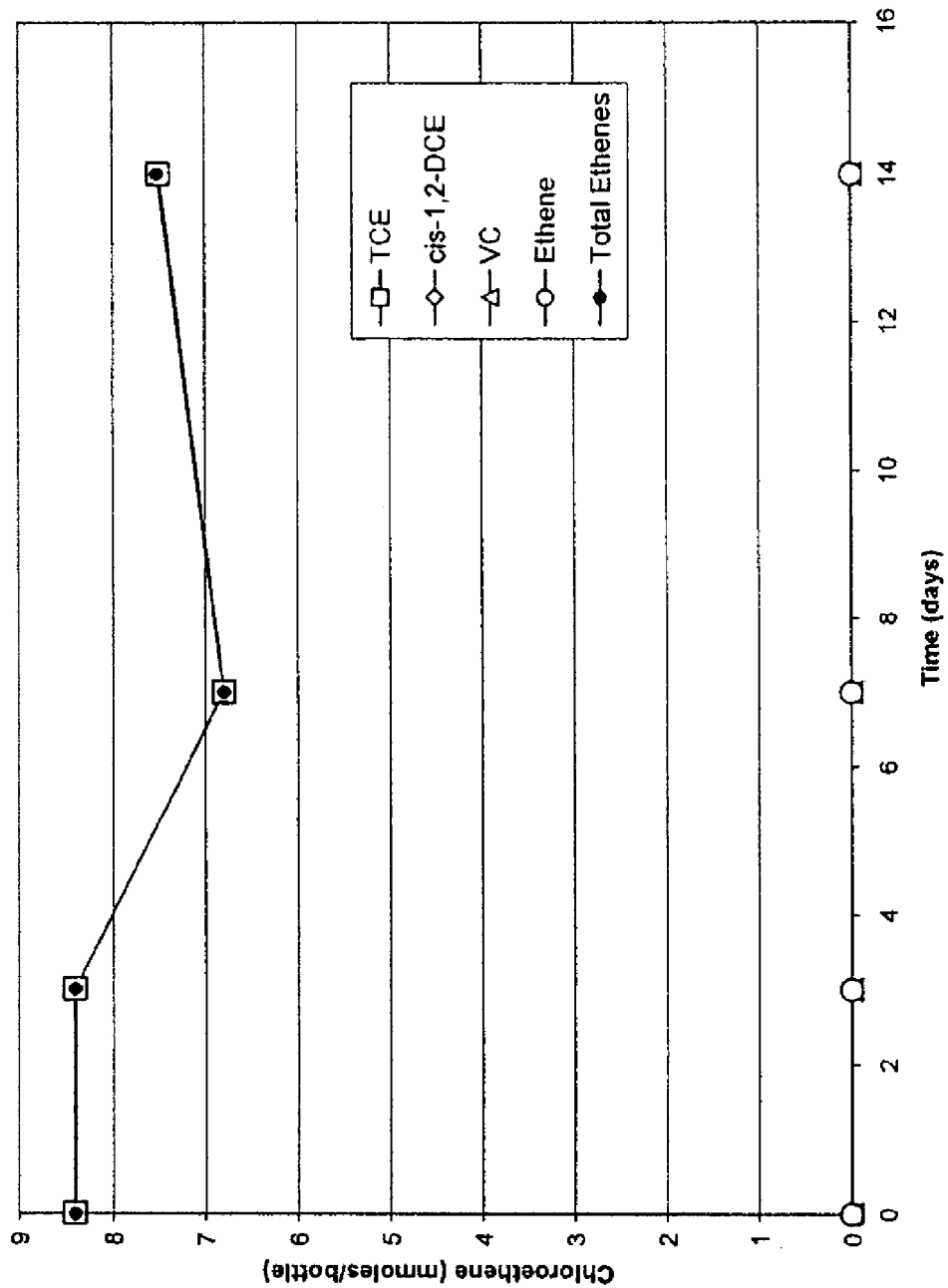
FIG. 5 shows the full analysis of the degradation of TCE by CAP18-ME as a control (Sample 2).
Figure 6:
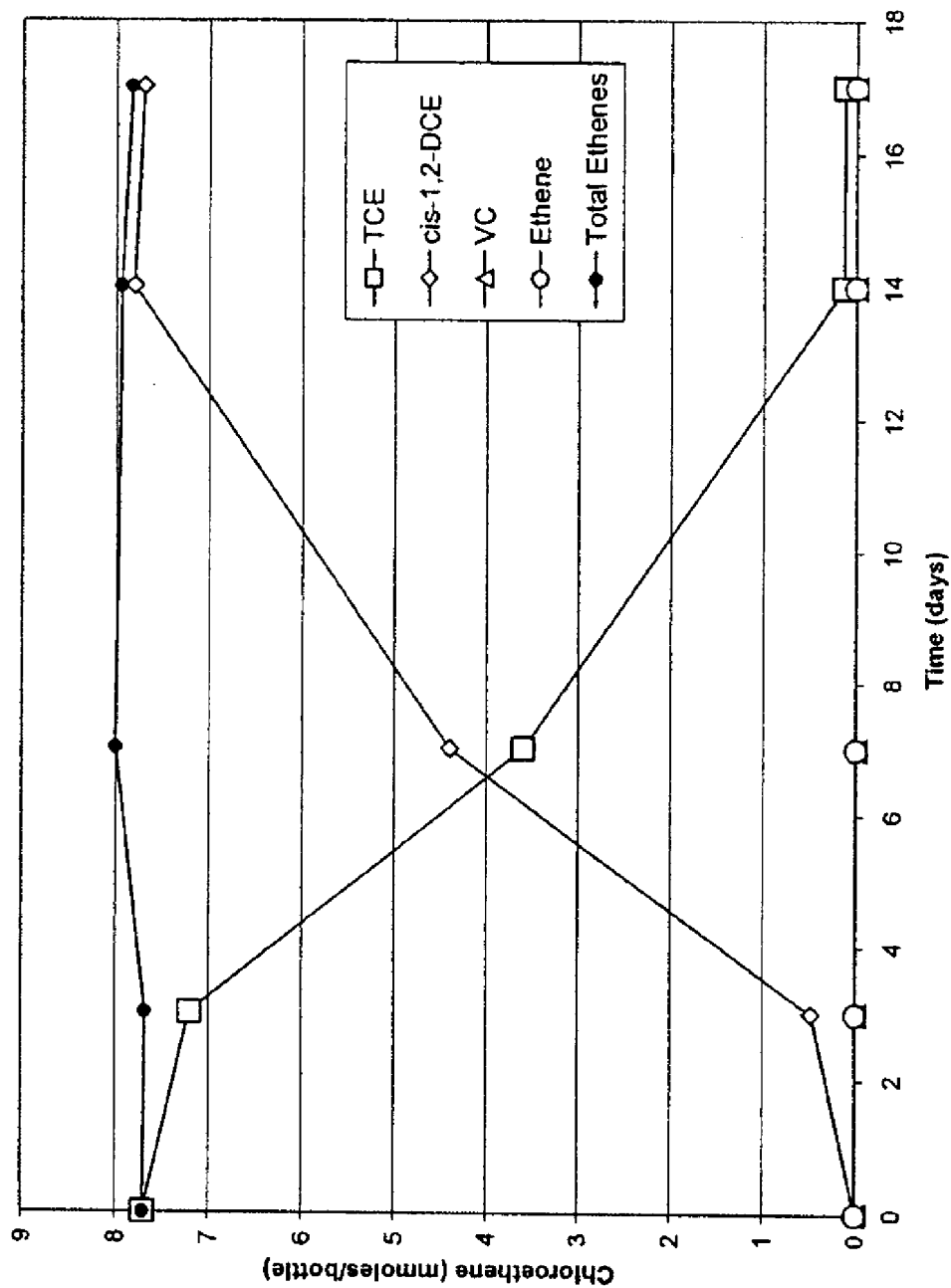
FIG. 6 shows the full analysis of the degradation of TCE by CAP18 bioaugmented with KB-1 (Sample 3).
Figure 7:
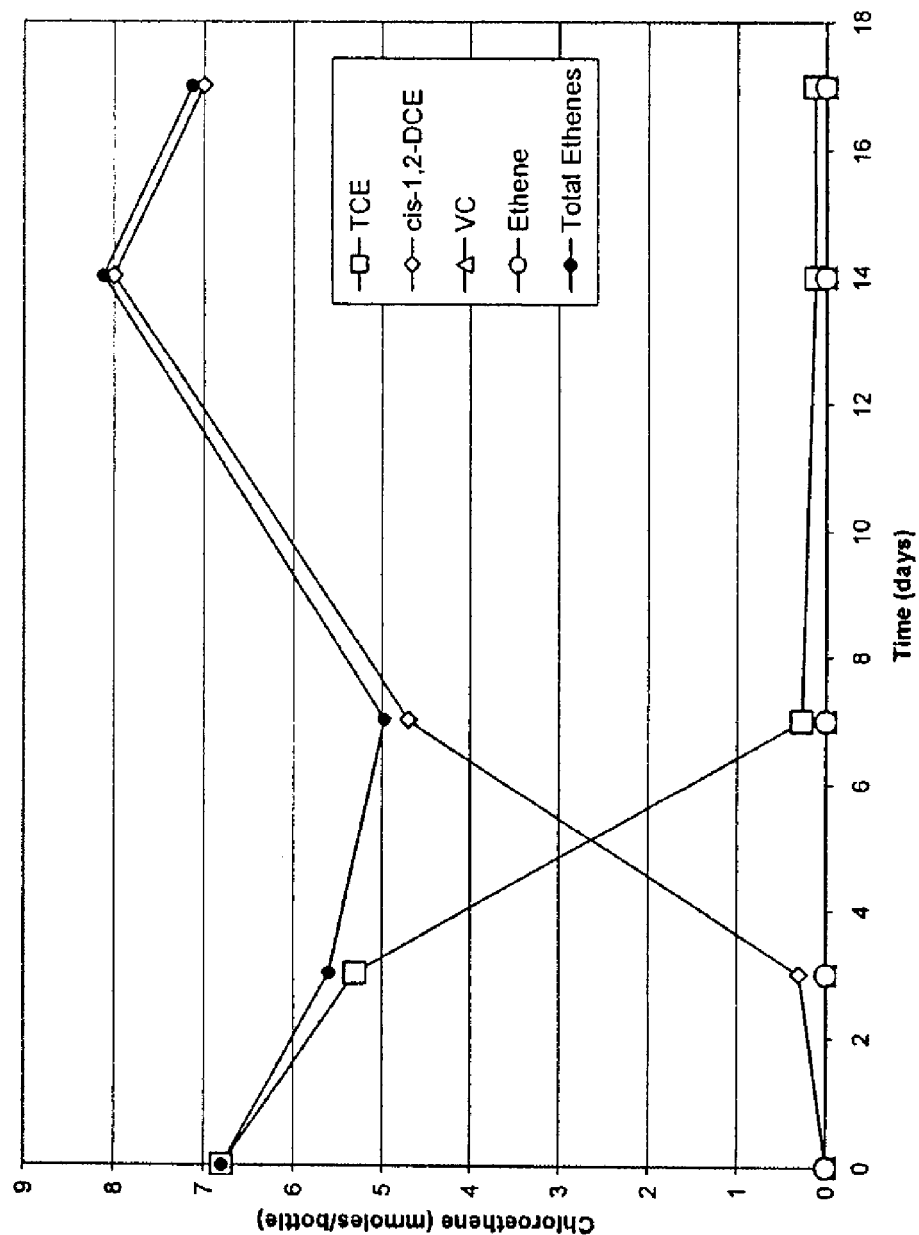
FIG. 7 shows the full analysis of the degradation of TCE by CAP18-ME bioaugmented with KB-1 (Sample 4).

A sample of CAP18 was converted into the corresponding methyl esters as described above. The GC-MS spectrum of the purified methyl esters is shown in FIG. 3, including the following components: hexadecanoic acid methyl ester (10.57), linoleic acid methyl ester (11.43); oleic acid methyl ester (11.45); octadecanoic acid methyl ester (11.53), at the indicated retention times.

CAP18-ME Compositions

Several compositions are prepared that include the methyl esters as prepared herein from CAP18 and CAP18 as available commercially in the following relative proportions by weight: (a) 91:9, (b) 90.5:8.5, (c) 90:10, (d) 89.5:10.5, (e) 89:11, (f) 88.5:11.2, and (g) 88:12.

Short-Term Microcosm Tests

The treatment and control microcosms listed in the following Table were constructed:

| Sample | Treatment/Control | Replicates | Innoculation |
|---|---|---|---|
| 1 | CAP18 [a] control | 2 | None |
| 2 | CAP18-ME control | 2 | None |
| 3 | CAP18 | 2 | KB-1 [b] |
| 4 | CAP18-ME | 2 | KB-1 [b] |

[a] CAP18 obtained from DBI Remediation Products, LLC (Fishers, IN, USA);
[b] KB-1 microbial population obtained from SiREM (Guelph, Ontario, Canada)

Microcosms were constructed by filling 250 milliliter (mL) (nominal volume) glass bottles with approximately 150 to 200 mL, typically 200 mL, of anaerobic mineral salts medium leaving a nominal headspace for gas production (e.g., ethene, carbon dioxide, methane). All treatments were constructed in duplicate. All microcosms were amended with TCE to reach desired target concentrations; for example, 1 mL of $H_2O$ saturated with TCE corresponds to a target TCE concentration of 5 mg/L. One replicate of each treatment is optionally amended with resazurin to monitor redox conditions. Resazurin is clear under anaerobic conditions but turns pink when exposed to oxygen. Microcosms were sealed with MININERT valves to allow repetitive sampling of each microcosm, to reduce the loss of volatile organic compounds (VOCs), and to allow addition of electron donors/acceptors to sustain metabolic/biodegradation activities as needed. In addition, bottles may be placed horizontally to further decrease the VOC loss through the closure. In order to maintain anaerobic conditions construction, storage and sampling of microcosms were conducted in an anaerobic chamber. The samples were incubated up to 99 days at ambient temperature (typically 20-22° C.).

The control microcosms, designed to measure intrinsic biodegradation activity, received electron donor amendments but were not bioaugmented with KB-1. Treatment microcosms were amended with electron donor at approximately 10 times the stoichiometric demand of the cVOCs and selected inorganic compounds (i.e., nitrate, sulfate and oxygen) or a concentration related to relevant field dosages. Microcosms were bioaugmented with a dehalorespiring microbial consortium (KB-1) at relevant field concentrations ($10^6$ cells per liter).

Figure 8:
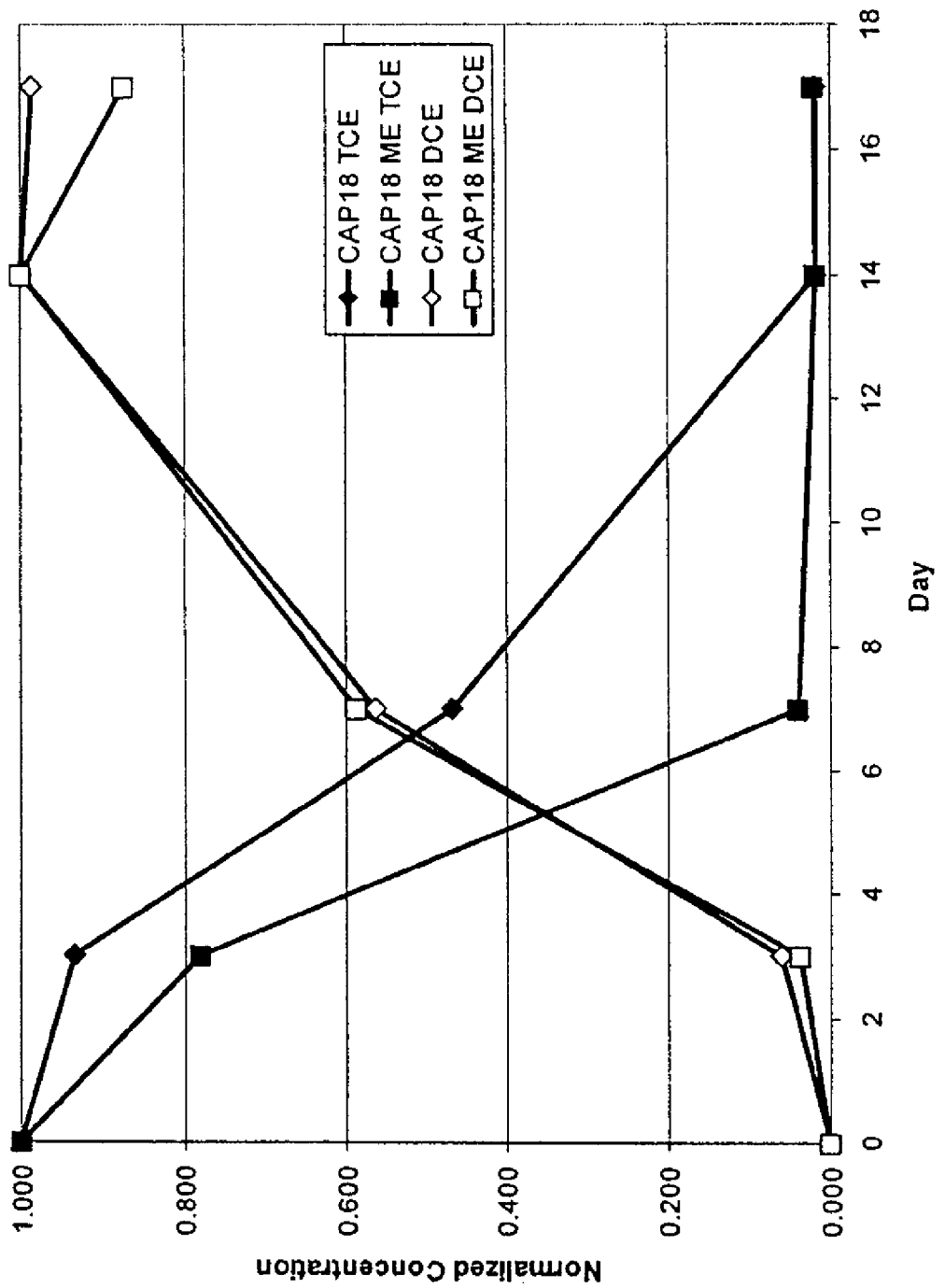
FIG. 8 shows the normalized degradation of TCE and cis-1,2-dichloroethene (DCE) by CAP18-ME compared to CAP18, each bioaugmented with KB-1 (Samples 3 and 4). Data were transformed by normalizing to the maximum concentration during the study period.

Microcosms were incubated for a period of 2 to 4 weeks. Aqueous samples were collected from the control and treatment microcosms every three to seven days for analysis of TCE and expected degradation intermediates (e.g., cis-DCE, VC) and end products (e.g., ethene, ethane). At two selected time points (beginning and end), samples were collected for analysis of added soluble electron donors (i.e., volatile fatty acids [lactate, acetate and propionate]). Other analyses included the measurement of pH, methane, and anions (i.e., sulfate, nitrate, chloride and phosphate). Sample intervals for individual treatments may be modified (either shorter or longer intervals) during the treatability study based on observed microbial activity, VOC degradation rates, and depletion of electron donors/acceptors. The results for the TCE degradation and each of the degradation products for the short-term study are shown in FIGS. 4-7. The normalized values for TCE and cis-1,2-DCE are shown in FIG. 8.

Long-Term Microcosm Tests

The treatment and control microcosms listed in the following Table were constructed:

| Sample [a] | Treatment/Control | Replicates | Innoculation |
|---|---|---|---|
| 5 | CAP18 [b] control | 2 | None |
| 6 | CAP18-ME control | 2 | None |
| 7 | CAP18 | 2 | KB-1 [c] |
| 8 | CAP18-ME | 2 | KB-1 |

[a] Samples were run in duplicate;
[b] CAP18 obtained from DBI Remediation Products, LLC (Fishers, IN, USA);
[c] KB-1 microbial population obtained from SiREM (Guelph, Ontario, Canada)

A total of 8 microcosms were constructed. Microcosms were constructed by filling sterile 250 milliliter (mL) (nominal volume) screw cap Boston round clear glass bottles (Systems Plus, New Hamburg, Ontario) with 200 mL of anaerobic mineral salt medium. Microcosms were spiked with 1 mL of a water saturated TCE stock (1100 milligrams per liter [mg/L]) to reach a target TCE concentration of approximately 5 mg/L. The bottles were capped with MININERT closures to allow repetitive sampling of the bottle with minimal VOC loss, and to allow amendments (addition of additional bioremediation compositions) as needed, throughout the incubation period. All control and treatment microcosms were constructed in duplicate.

All microcosms were sampled and incubated in an anaerobic chamber (Coy Laboratory Products, Grass Lake, Mich.) filled with approximately 80% nitrogen, 10% carbon dioxide, and 10% hydrogen (BOC gases). Hydrogen was present to scavenge low levels of oxygen via a palladium catalyst, and anaerobic conditions were verified by an open bottle of resazurin-containing mineral medium, which turns pink if oxygen is present. During quiescent incubation, all microcosms were covered to minimize photodegradation, and placed horizontally to minimize VOC losses via the (submerged) MININERT closure. Microcosms were incubated for a period of up to 99 days at 22° C. (room temperature).

CAP18 and CAP18-ME were evaluated. Two sets of duplicate microcosms were prepared for each electron donor formulation. On Day (-1), 100 microliters (μL) of the CAP18 formulations were added to the respective treatments corresponding to 0.05% CAP18 on a volume per volume basis or approximately 460 mg/L CAP18.

To assess the ability of the two formulations to act as electron donors for biostimulation to dechlorinate TCE to ethene, one set of each electron donor treatment was bioaugmented with KB-1 culture on Day 0. Microcosms were bioaugmented to a target Dehalococcoides concentration of $10^6$ cells per liter (cells/L) in the microcosms. To achieve this cell concentration, a 1 mL aliquot of a culture with a steady state concentration of approximately 1011 Dehalococcoides cells/L (determined by monthly Gene-Trac testing) was serially diluted 3 times in 9 mL of anaerobic mineral medium. Adding 2.0 mL of the diluted cell suspension to each 200 mL microcosm resulted in a 5 order-of-magnitude reduction in Dehalococcoides concentrations compared to the parent culture.

Aqueous samples were collected from the control and treatment microcosms on a weekly to biweekly (i.e., every two weeks) basis for analysis of VOCs (TCE, cis-1,2-DCE, and VC) and dissolved hydrocarbon gases (DHGs) (ethene, ethane, and methane). Microcosms were sampled using gastight 1 mL Hamilton glass syringes. Separate sets of syringes were used for bioaugmented and non-bioaugmented treatments to reduce the potential for transfer of KB-1 microorganisms to non-bioaugmented treatments. Syringes were cleaned with acidified water (pH ~2) and rinsed 10 times with deionized water between samples, to ensure that VOCs and microorganisms were not transferred between different samples or treatments. The analytical methods employed by SiREM are described below.

Analysis of VOCs (chlorinated ethenes) and Dissolved Hydrocarbon Gases (DHGs). The quantitation limits (QL) for the chlorinated ethenes, ethanes, and methanes and DHGs were typically 10 micrograms per liter (μg/L) in the microcosm based on the lowest concentration standards that were included in the linear calibration trend.

Aqueous VOC concentrations in the microcosms were measured using a Hewlett-Packard (Hewlett Packard 5890 series II Plus) gas chromatograph (GC) equipped with an auto sampler (Hewlett Packard 7684) programmed to heat each sample vial to 75° C. for 45 min prior to headspace injection into a GSQ Plot column (0.53 mm×30 m, J&W) and a flame ionization detector. Sample vials were heated to ensure that all VOCs in the aqueous sample would partition to the headspace. The injector temperature was 200° C., and the detector temperature was 250° C. The oven temperature was programmed as follows: 35° C. for 2 min, increase to 100° C. at 50 degrees Celsius per minute (° C./min), then increase to 185° C. at 25° C./min and hold at 185° C. for 5.80 min. The carrier gas was helium at a flow rate of 11 milliliters per minute (mL/min).

After withdrawing a 1.0 mL sample (as previously described), the sample was injected into a 10 mL auto sampler vial containing 5 mL of acidified deionized water (pH ~2). The water was acidified to inhibit microbial activity between microcosm sampling and GC analysis. The vial was sealed with an inert Teflon-coated septum and aluminum crimp cap for automated injection of 3 mL of headspace onto the GC. One VOC standard was analyzed with each batch of samples to verify the yearly fivepoint calibration using methanolic stock solutions containing known concentrations of the target analytes. Calibration was performed using external standards that were purchased as standard solutions (Sigma). Known volumes of standard solutions were added to acidified water in auto sampler vials and analyzed as described above for microcosm samples. Data were integrated using Peak Simple Chromatography Data System Software (SRI, Inc.). Concentrations were converted from mg/L to total millimoles per bottle using Henry's Law.

Figure 9A:
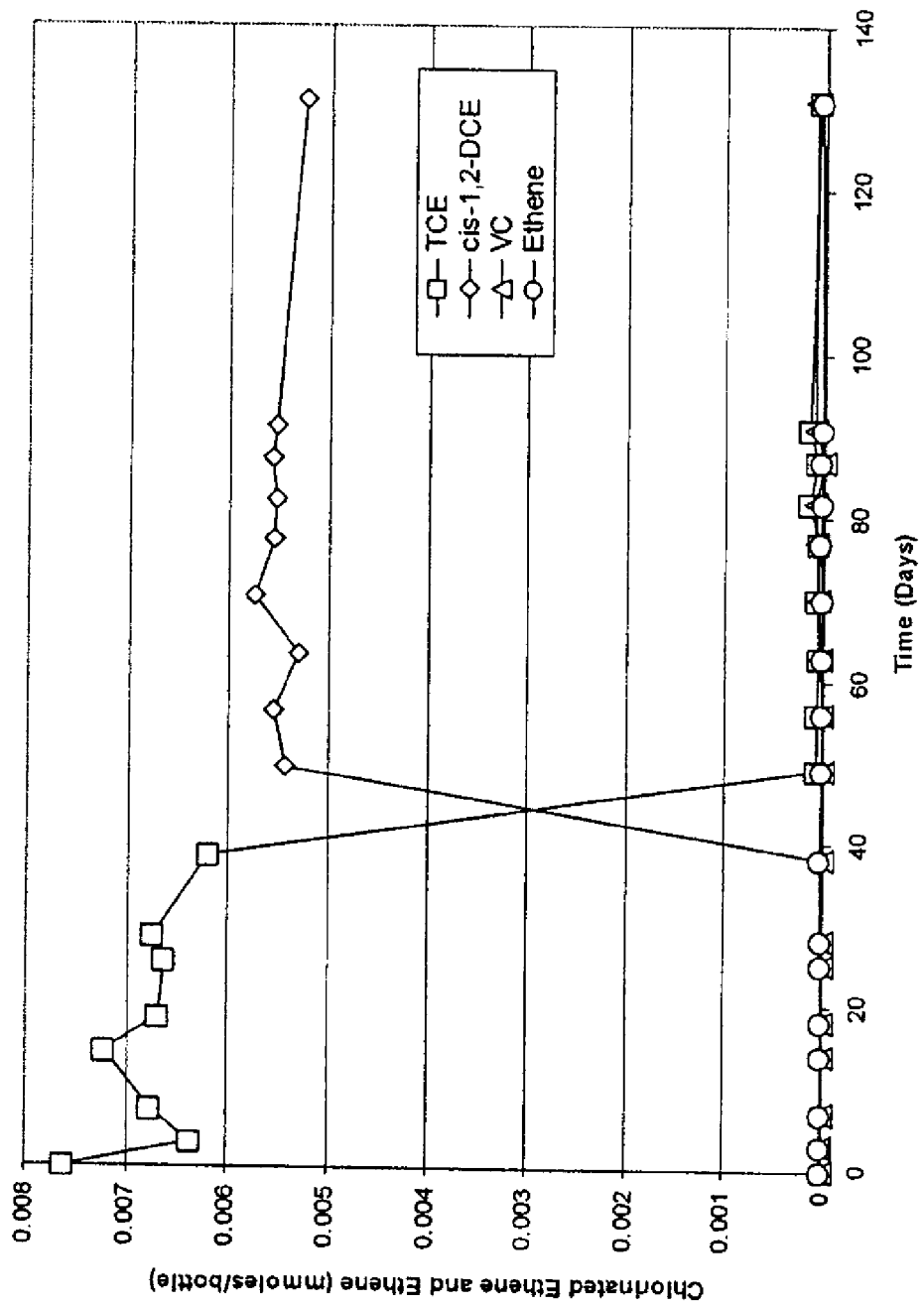
FIGS. 9(a) and 9(b) show replicates of two experiments showing the full analysis of the degradation of TCE by CAP18 as a control (Sample 5). Replicate 1 (FIG. 9(a)) showed contamination by dechlorinating bacteria and subsequent degradation of TCE to cis-1,2-DCE; Replicate 2 (FIG. 9(b)) showed stable concentrations of TCE with no degradation.
Figure 9B:
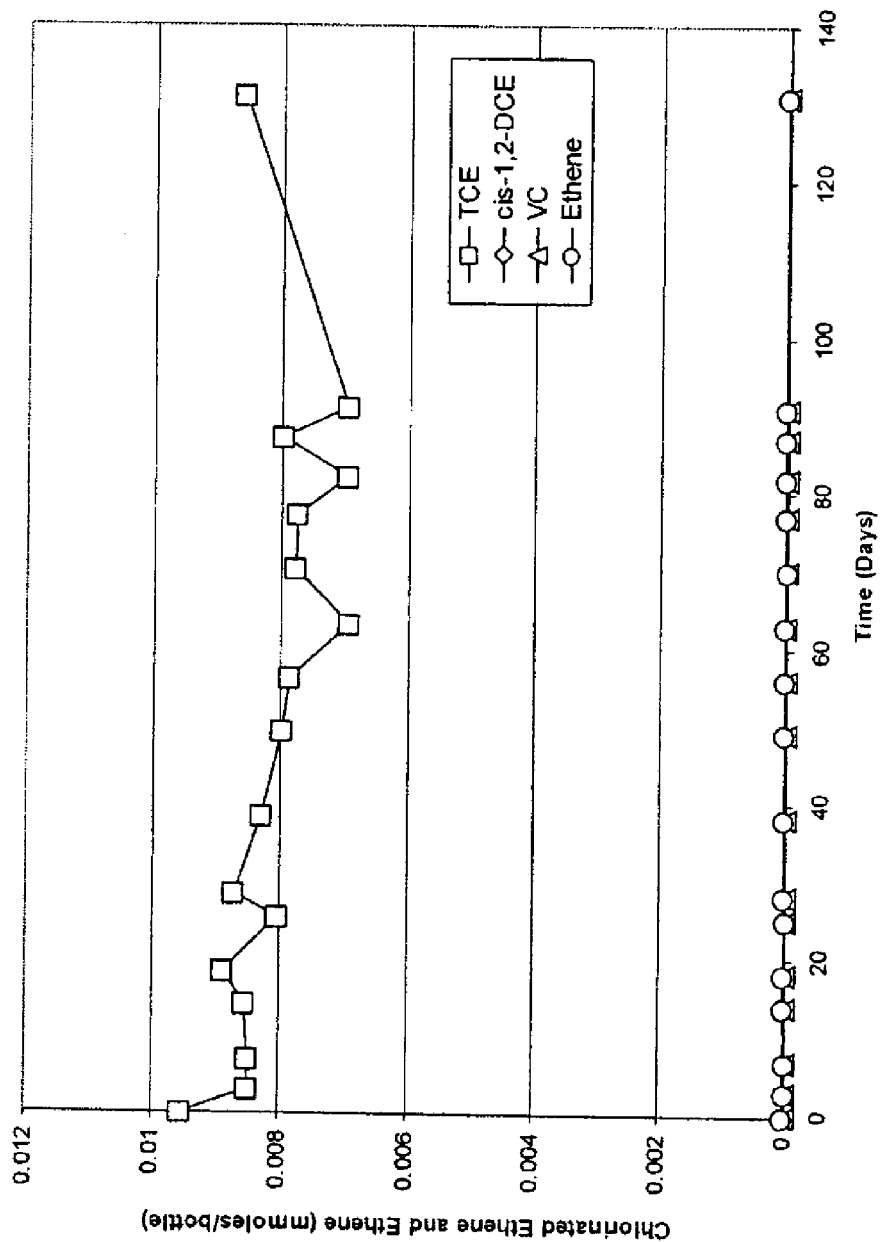

The chlorinated ethene concentrations in the CAP18 amended control microcosm (replicate #2) remained stable over the incubation period, showing no decline in TCE concentrations as well as no increase in cis-1,2-DCE, VC or ethene concentrations (FIG. 9(b)). After day 40, in replicate #1 there was conversion of TCE to cis-1,2-DCE in indicating contamination with dechlorinating bacteria capable of reductive dechlorination of TCE to cis-1,2-DCE (FIG. 9(a)). Although every possible attempt was made to avoid contamination, it is possible that there was cross contamination during feeding or sampling of the microcosm bottles. Replicate #2 showed no losses of TCE and a consistent mass balance over the 131 day incubation period. Each of the results shown in FIGS. 9(a) and 9(b) are from separate microcosm bottles.

Figure 10:
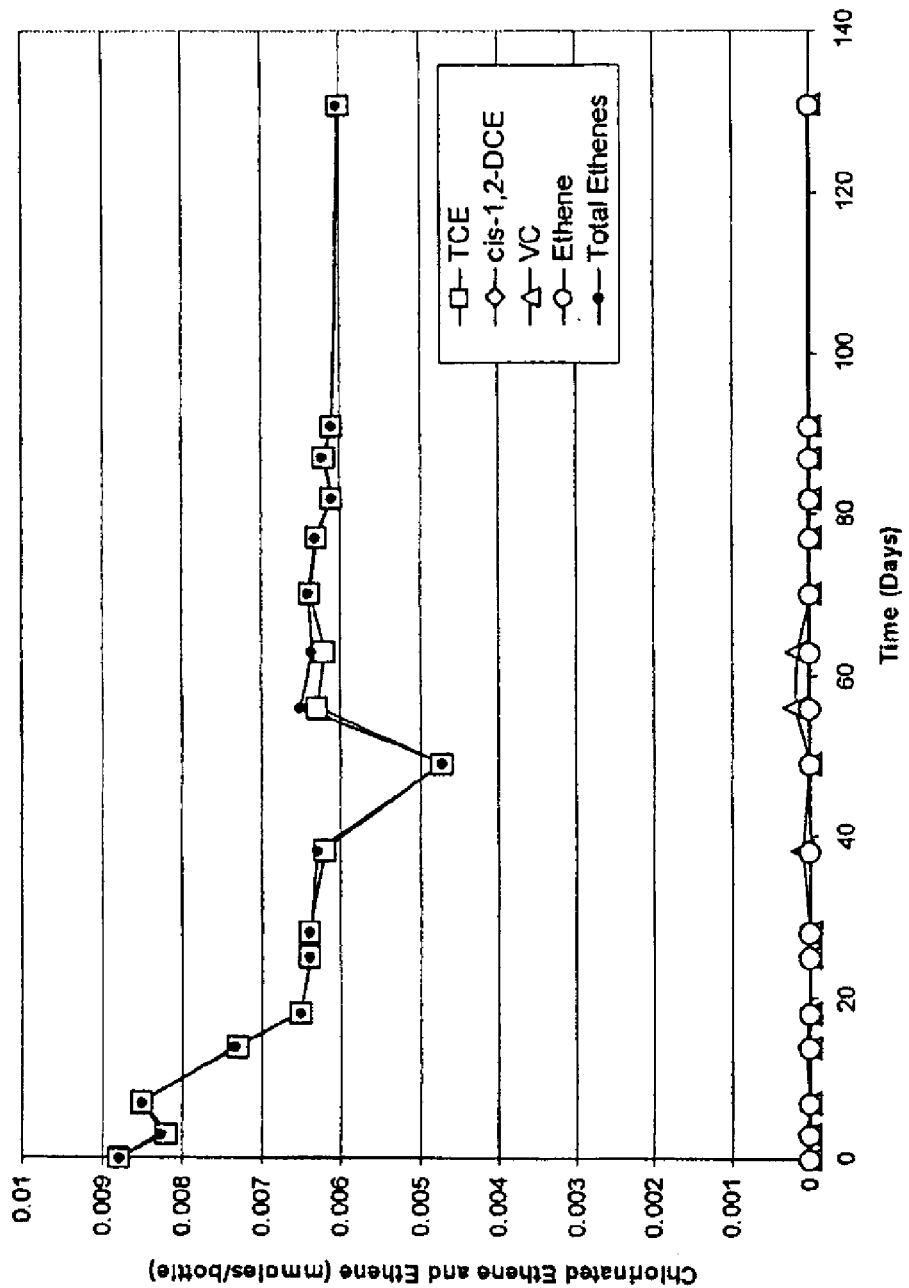
FIG. 10 shows the full analysis of the degradation of TCE by CAP18-ME as a control (Sample 6).
Figure 11:
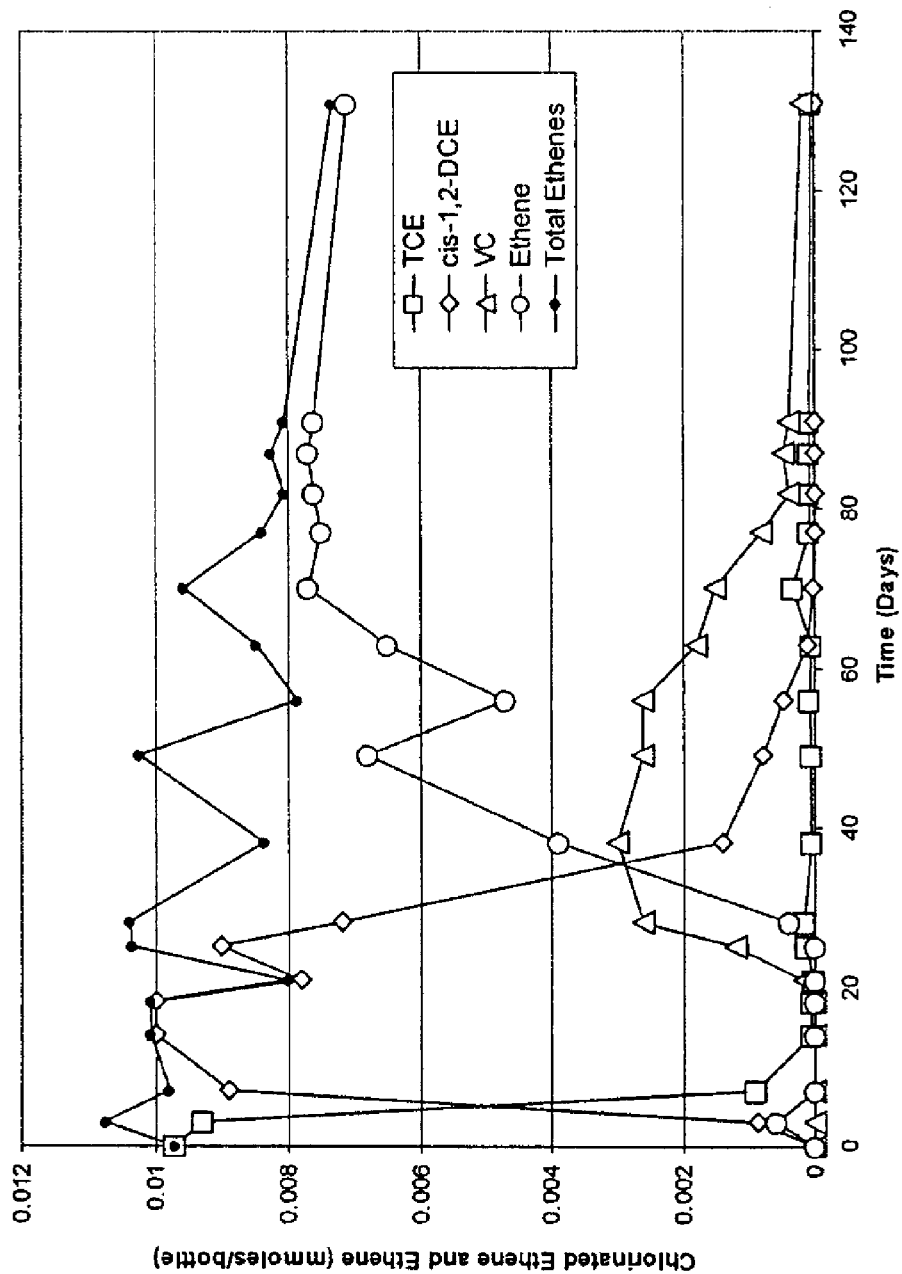
FIG. 11 shows the full analysis of the degradation of TCE by CAP18 bioaugmented with KB-1 (Sample 7).

The TCE concentration in the CAP18-ME amended control microcosms decreased slightly up to day 38, but there was no increase in cis-1,2-DCE, VC or ethene concentrations (FIG. 10). This decrease in TCE concentration is likely related to sorption of the TCE into the oil component of the CAP18-ME electron donor. The TCE concentrations remained stable over the remainder of the incubation period, showing no decline in TCE concentrations as well as no increase in cis-1,2-DCE, VC or ethene concentrations (FIG. 10).

All chlorinated ethene and ethene concentrations are presented in units of mg/L and millimoles per microcosm bottle (mmol/bottle) to demonstrate mass balances on a molar basis. FIGS. 9-12 present trends in the concentrations of chlorinated ethenes and ethene in the control and treatment microcosms over the incubation period for the study. The data plotted are from averages of duplicate microcosms, except for FIGS. 9(a) and 9(b), which are each plotted from a single microcosms.

Figure 13A:
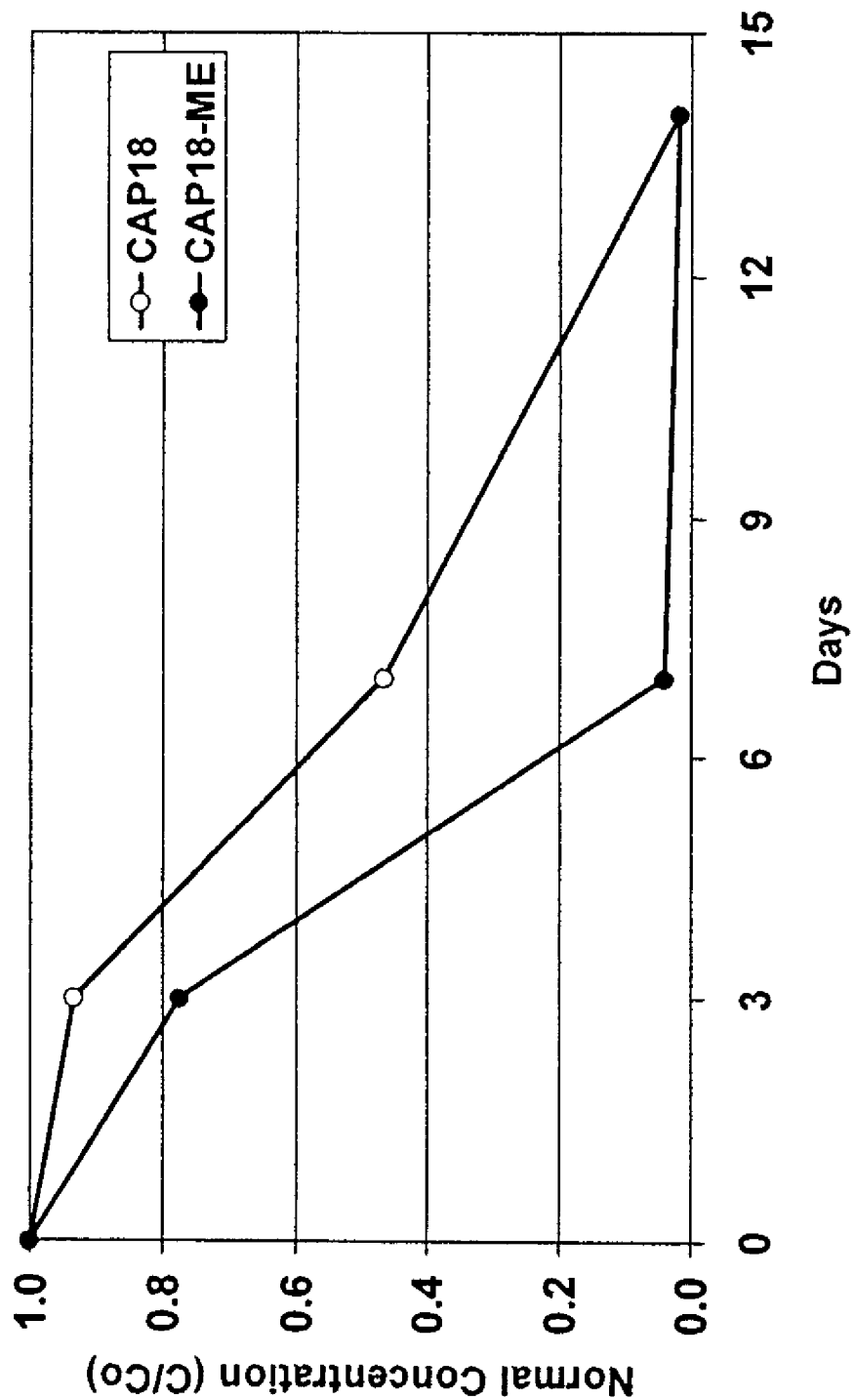
FIGS. 13(a) and 13(b) show replicates of two experiments showing the normalized degradation of TCE by CAP18-ME compared to CAP18, each bioaugmented with KB-1 (Samples 7 and 8).
Figure 13B:
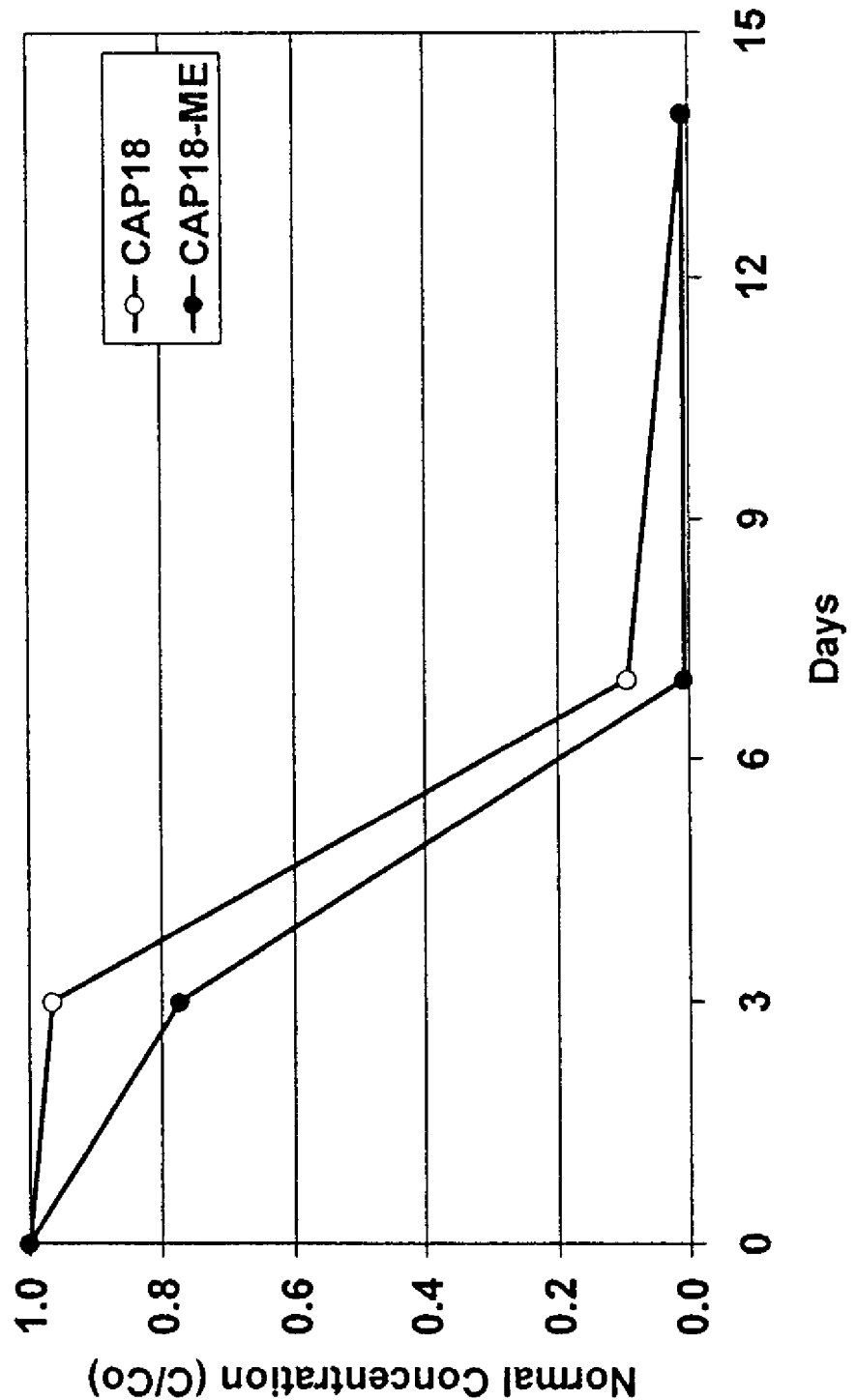

The normalized concentrations for comparing CAP18 and CAP18-ME are shown in the FIGS. 13(a) and 13(b) for the microcosms that were bioaugmented with KB-1. As shown in FIGS. 13(a) and 13(b), TCE degradation began more quickly with CAP18-ME than with CAP18. TCE was degraded approximately 50% faster with CAP18-ME than with CAP18. Average TCE degradation rates (k) were 0.34/day (corresponding to a $t_{1/2}$ of 2.1 days for CAP18, and 0.70/day (corresponding to a $t_{1/2}$ of 1.1 days) for CAP18-ME. After the first 10-20 days, differences between the degradation rates are less pronounced. As shown, TCE dechlorination began without delay and a corresponding increase in cis-1,2-DCE was observed for both CAP18 and CAP18-ME.

Figure 14:
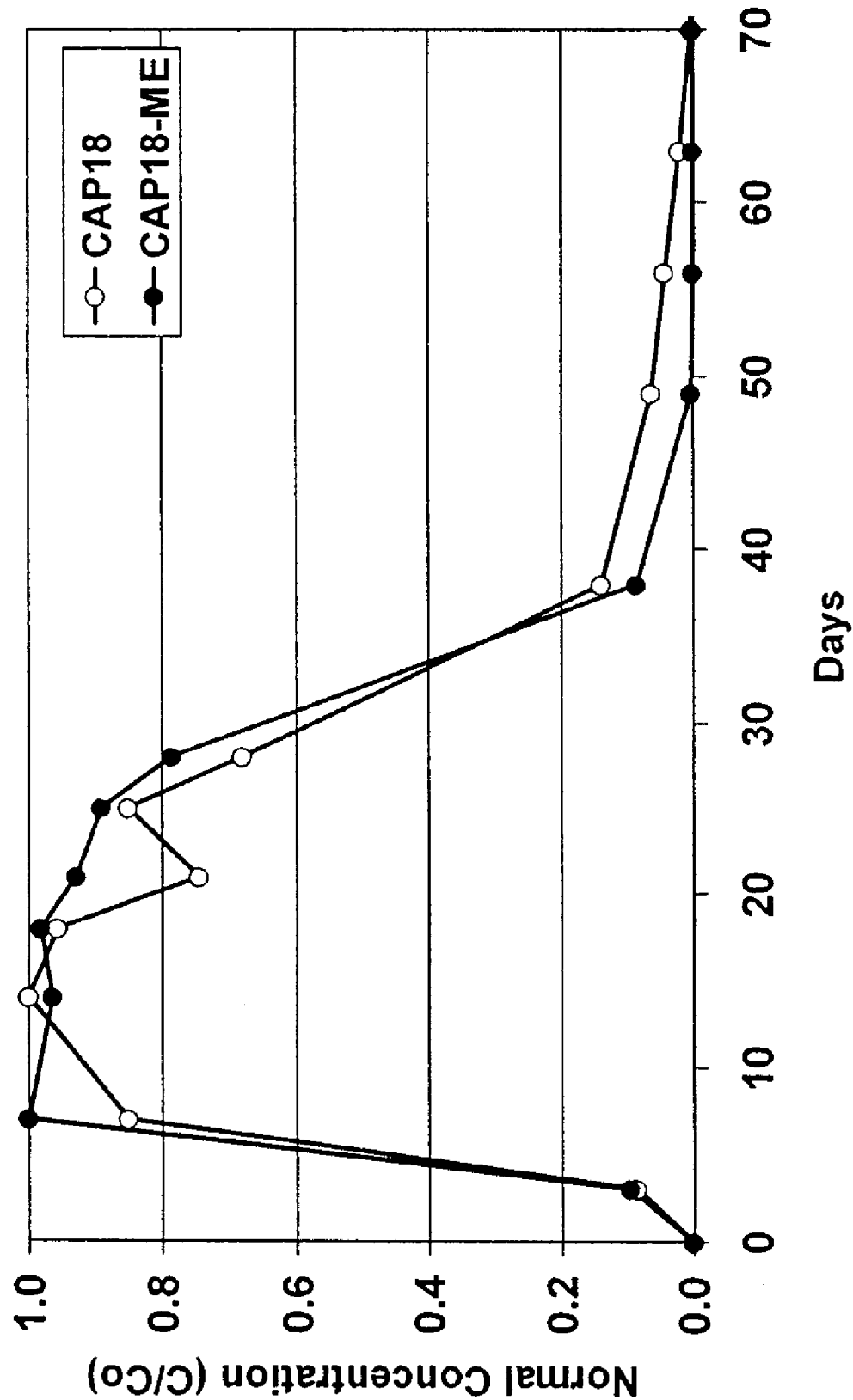
FIG. 14 shows the normalized degradation of cis-1,2-DCE by CAP18-ME compared to CAP18, each bioaugmented with KB-1.

Referring to FIG. 14, the degradation rates for cis-1,2-DCE by CAP18 and CAP18-ME are shown. Evolution of cis-1,2-DCE in the microcosm was similar for both compounds. However, the peak concentration of cis-1,2-DCE was reached earlier with CAP18-ME reflecting the faster degradation of the precursor TCE. The final degradation occurred more rapidly with CAP18-ME than with CAP18.

For CAP18, cis-1,2-DCE began to decrease after day 18 with a corresponding increase in VC and ethene. For CAP18-ME, cis-1,2-DCE began to slowly decrease after day 7, but VC was not detected until day 21. However, for CAP18-ME, cis-1,2-DCE began to rapidly decrease after day 25 and reached non-detect by day 49 with corresponding increases in VC and ethene.

Figure 15:
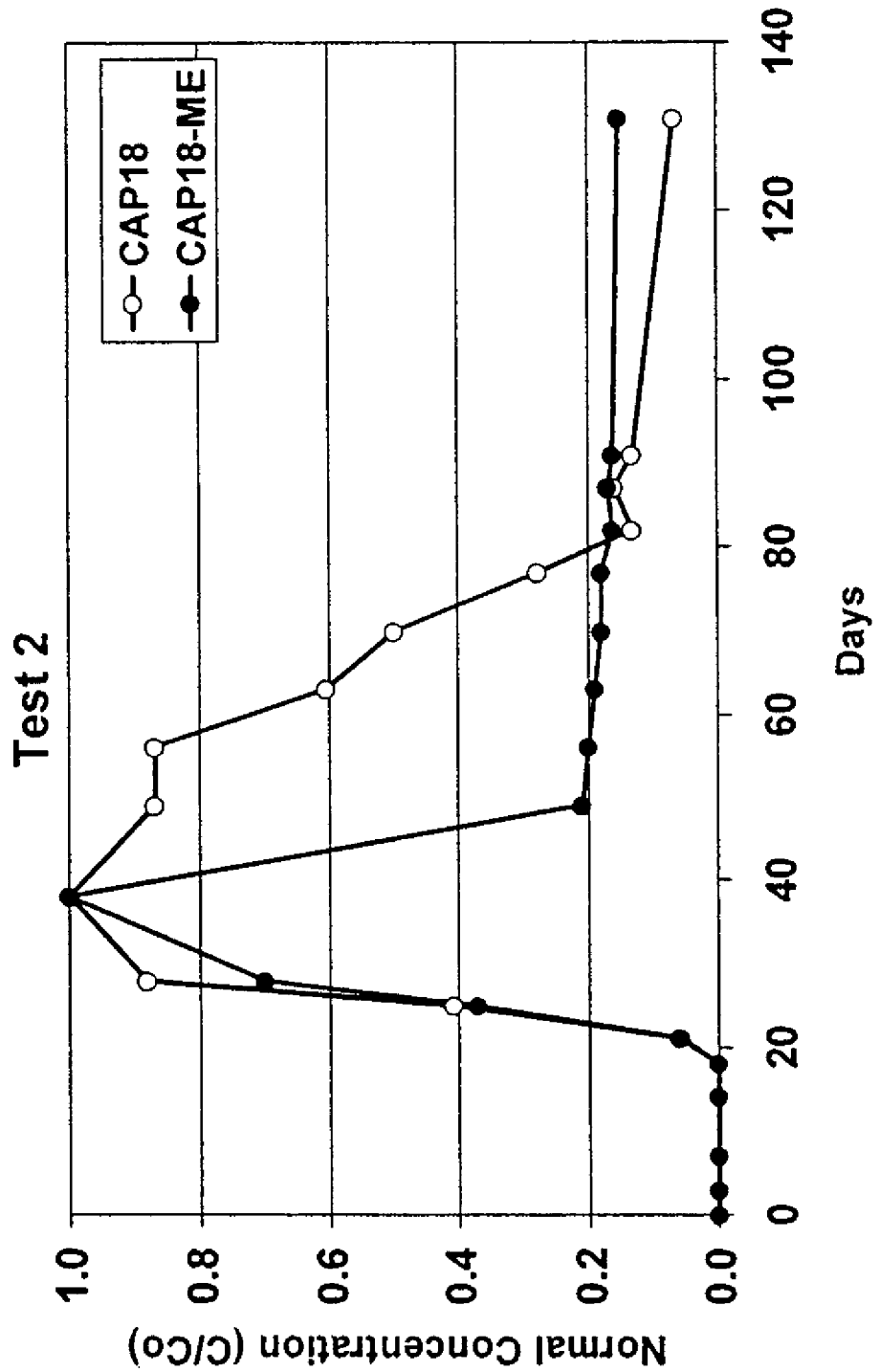
FIG. 15 shows the normalized degradation of vinyl chloride (VC) by CAP18-ME compared to CAP18, each bioaugmented with KB-1.
Figure 16:
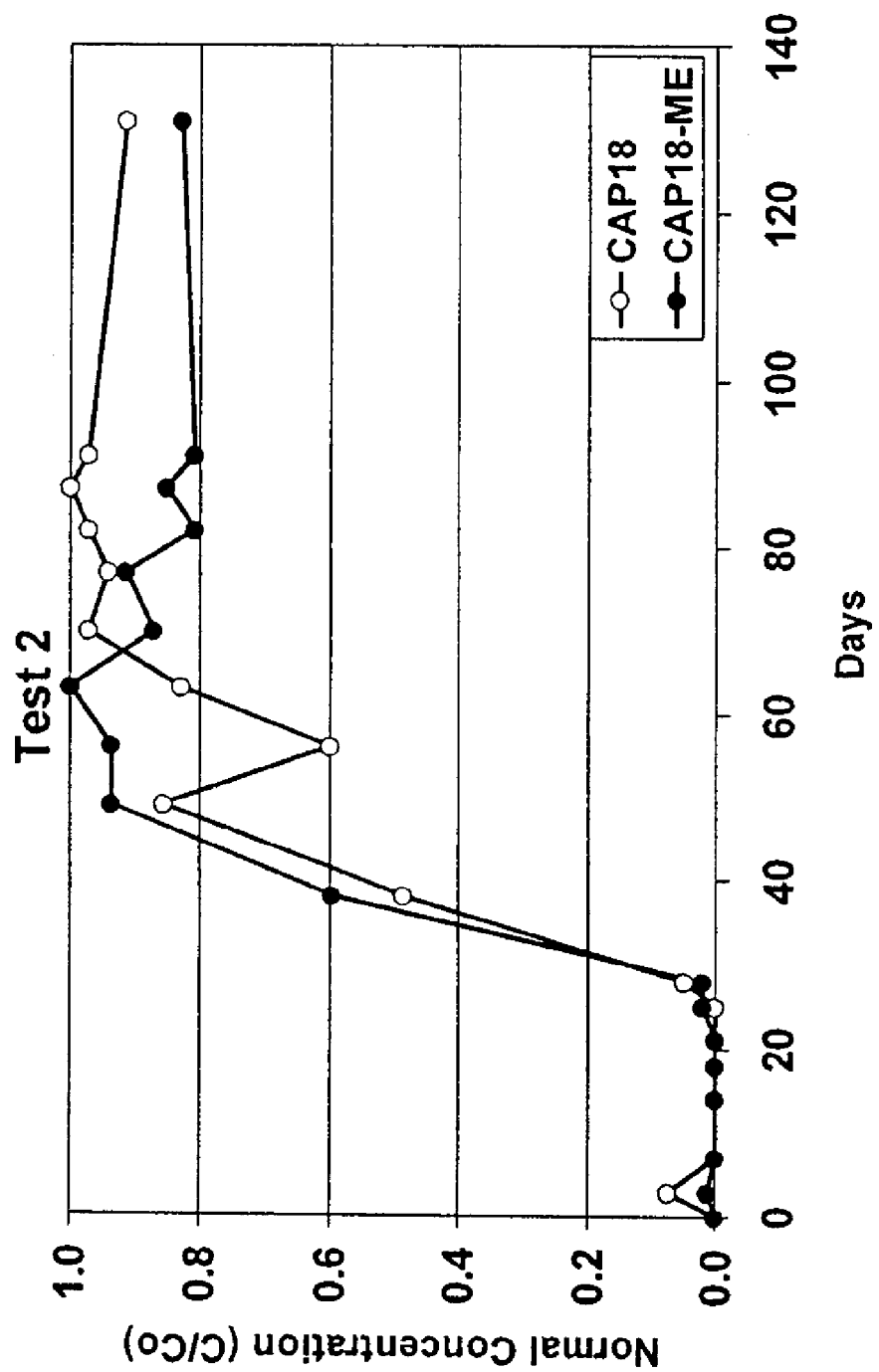
FIG. 16 shows the normalized production of ethene by CAP18-ME compared to CAP18, each bioaugmented with KB-1.

As shown in FIGS. 15 and 16, similar degradation patterns between CAP18 and CAP18-ME were observed for both VC and ethane. CAP18-ME exhibited an initially faster cis-1,2-DCE and VC degradation rate than CAP18, which led to an earlier achievement of peak concentrations of the product, VC and ethene, respectively. Further, the degradation rates from the peak were more rapid with CAP18-ME than with CAP18.

For CAP18, VC concentrations began to decrease after day 56 and ethene concentrations continued to increase. VC slowly decreased over the remainder of the incubation period reaching near non-detect levels by the end of the 131 day incubation period. For CAP18-ME, VC concentrations decreased between days 38 and 49 and ethene concentrations continued to increase. After day 49 VC slowly decreased over the remainder of the incubation period reaching near non-detect levels by the end of the 131 day incubation period. The VC concentrations at the end of the study were slightly higher in this treatment then in the CAP18 treatment microcosms.

Henry's Law Calculations

The following Henry's Law calculation was used to convert aqueous concentrations to total mmoles of each analyte per microcosm bottle:

$$\text{Total } mmoles = \frac{C_{liq} \times (V_{liq} + H \times V_{gas})}{\text{Molecular Weight (mg/mmol)}}$$

where $C_{liq}$ is the liquid concentration (mg/L); $V_{liq}$ is the liquid volume (0.18 L) per bottle; $V_{gas}$ is the headspace volume (0.04 L) per bottle; and H is Henry's Law constant (dimensionless). The Henry's Law constants used are summarized in the following Table:

| Analyte | Henry's Law Constant [a] |
|---|---|
| Trichloroethene | 0.48 |
| cis-1,2-dichloroethene | 0.31 |
| Vinyl chloride | 0.95 |
| Ethene | 8.76 |
| Methane | 27.2 |

[a] Montgomery, J. H. 2000. Groundwater Chemicals Desk Reference, Third Edition. CRC Press LLC, Boca Raton, FL.

Half-Life Calculations

The following calculation was used to determine dechlorination half lives in the microcosm study. The dechlorination half life is the time required to decrease the concentration by one half of its initial value, according to the following formula:

$$t_{1/2} = \ln(2)/k$$

where ln(2) is the natural logarithm of 2; k is the first order rate constant, according to the following formula:

$$k = \frac{\ln(\text{initial concentration}) - \ln(\text{final concentration})}{\text{elapsed time (days)}}.$$

where the rate constant (k) is calculated by selecting the sampling point with the highest concentration of a particular species as the initial concentration and the sampling point with the lowest concentration as the final concentration (or one half of the detection limit if the concentration has decreased below the detection limit). The difference in days between these two sampling points is used as the elapsed time.

Figure 12:
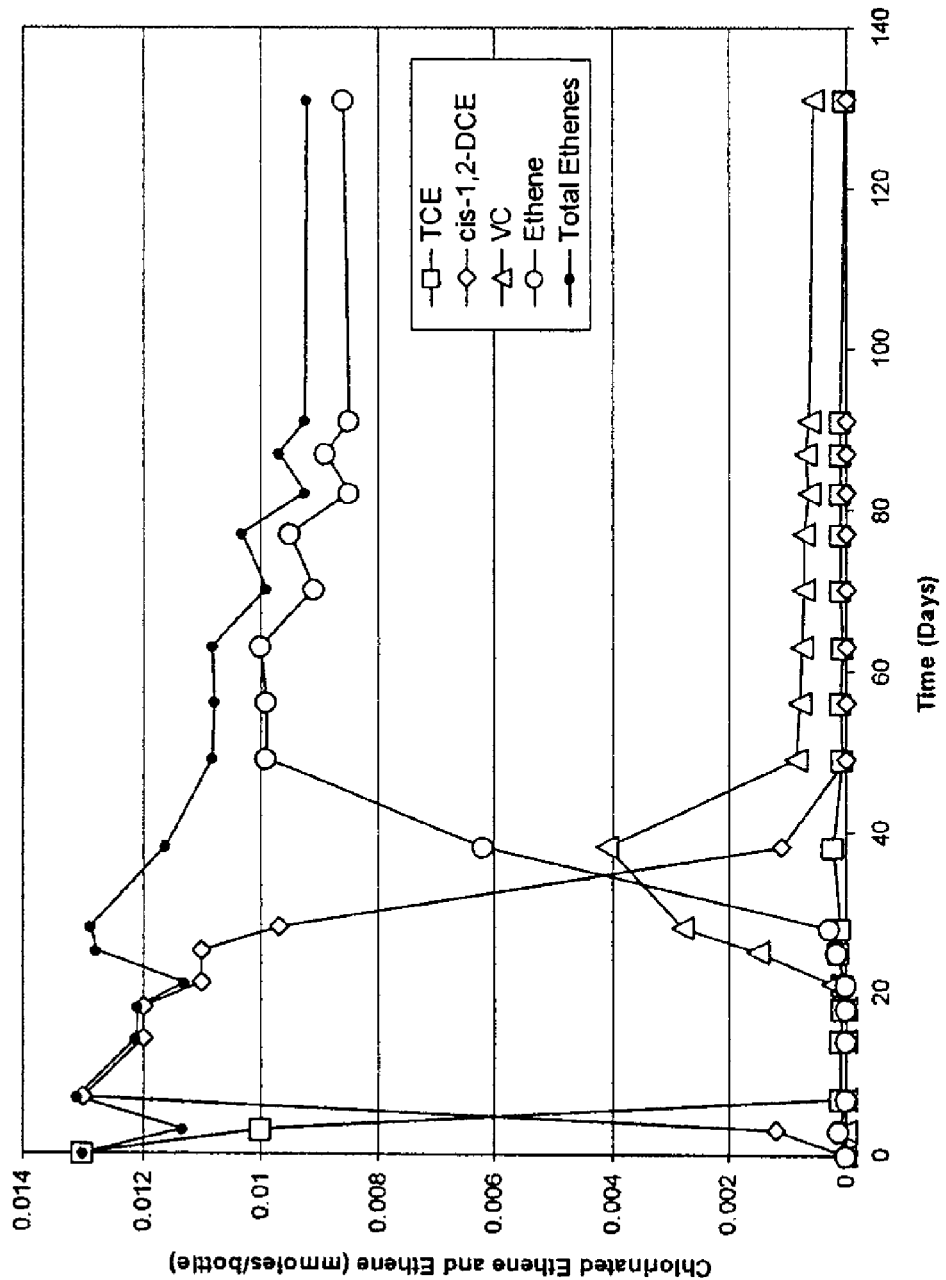
FIG. 12 shows the full analysis of the degradation of TCE by CAP18-ME bioaugmented with KB-1 (Sample 8).

For example, for cis-1,2-DCE from the CAP18-ME/KB-1 Amended Treatment microcosms. As shown in FIG. 12, the TCE has been completely converted to cis-1,2-DCE by day 7. Therefore, the concentration of cis-1,2-DCE at day 7 is chosen as the initial concentration. By day 49, essentially all of the cis-1,2-DCE has been dechlorinated; therefore, the concentration of cis-1,2-DCE at day 49 is chosen as the final concentration. The elapsed time for dechlorination is the difference between these two time points (49−7=42 days).

$k$=[ln(0.013 mmoles/bottle)−ln(0.000013 mmoles/bottle)]/42 days=0.1636 days$^{-1}$ $t_{1/2}$=ln(2)/0.1636 days$^{-1}$=4.2 days Therefore, the dechlorination half-life for cis-1,2-DCE in the CAP18-ME amended/KB-1 treatment microcosms is calculated to be 4.2 days$^{-1}$. Additional data is shown in the following Table:

Half lives (days) of chlorinated ethenes detected in microcosms.

| TCE | Half Life (Days) | Initial Day [a] | Final Day [b] |
|---|---|---|---|
| CAP18/KB-1 | 2.0 | 0 | 7 |
| CAP18-ME/KB-1 | 1.0 | 0 | 7 |

| cis-1,2-DCE | Half Life (Days) | Initial Day | Final Day |
|---|---|---|---|
| CAP18/KB-1 | 6.3 | 14 | 70 |
| CAP18-ME/KB-1 | 4.2 | 7 | 49 |

| VC | Half Life (Days) | Initial Day | Final Day |
|---|---|---|---|
| CAP18/KB-1 | 24 | 38 | 131 |
| CAP18-ME/KB-1 | 34 | 38 | 131 |

[a] Initial day is the day in the study that the initial concentration is taken for the half life calculation;
[b] Final day is the day in the study that the final concentration is taken for the half life calculation Direct-Push Injection Application into a Subsurface Formation Injection is usually accomplished via a pressurized system to deliver the required volume of the compositions described herein. A number of manufacturers offer direct-push equipment that can be utilized for injection. For example, using GEOPROBE equipment. The Pressure-Activated Injection Probe can be utilized with either 1.5-inch probe rods (part no. 21479) or with 1.25-inch probe rods (part no. 18735). The probe can be used for "top-down" or "bottom-up" injection. Injection Pull Caps (part no. 16697 for 1.25-inch rods and 16698 for 1.5-inch rods) provide a means to make a sealed connection to the probe rods for injection while retracting the probe rod string. As an alternative to the use of the Pressure-Activated Injection Probe, injection can also be accomplished "bottom-up" through the Geoprobe® rods using an expendable drive point tip. Pressurized injection may be required to deliver sufficient composition. One method to deliver the composition is to utilize a grout pump, such as the GEOPROBE GS2000 series pump. The composition may be transferred from a drum to the pump hopper with a drum pump, diaphragm pump, or centrifugal pump. Alternatively, a diaphragm pump (such as the Yamada NDP-15) can be fit to draw directly from a drum and connect to the probe rods. Santoprene, Buna-N, Viton, and PTFE diaphragm materials may be used. After positioning the GEOPROBE and attaching the tooling, the probe is pushed to the target depth and injection begins. The injection can be conducted from the bottom-up, or from the top-down. Advance or withdraw the rods slowly during injection, while monitoring delivery volume, to ensure delivery of the desired composition volume to the target zones. After removal of all tooling, fill the boring to grade with bentonite or cement, or otherwise as required by local regulations. It is understood that the exact procedures utilized in the field will, of course, vary based upon the equipment staged onsite, unique site conditions, and project design.

Injection Application into a Subsurface Formation Via a Permanently-Installed Monitoring or Injection Well The composition may be injected through standard monitoring wells, or injection wells installed specifically for the purpose of composition injection. Wells can be installed with hollow-stem auger, direct-push, air rotary, or other standard methods. Generally, the compositions are generally compatible with commonly used well construction materials (PVC, stainless steel). Wells should be installed with no more than 10 feet of screen to prevent preferential injection of the composition to a narrow stratigraphic interval. The annular space above the screened interval should be sealed with tremied Portland cement grout to provide a competent seal. Allow sufficient riser at the surface to attach a PVC fitting; utilize a relatively large well vault (10-12 inches) to provide sufficient clearance in flush mount wells. A packer system may not be recommended for pressurized injection of the composition, because the composition may diminish the packer seal integrity, potentially resulting in slippage from the well. Glue (PVC) or weld (stainless steel) a threaded fitting to the well riser pipe. The hose from the injection pump should be threaded to the well head. Teflon tape may be used for a leak-tight fitting. The compositions generally are compatible with standard hose materials, including PVC, polyethylene, metal pipe, nylon, polypropylene, Buna-N (nitrile), and silicone. Natural rubber may be avoided. Double-diaphragm pumps such as the Yamada NDP series are very effective for pressure injection of the composition (Santoprene Buna-N, Viton®, or PTFE diaphragm material is acceptable). Centrifugal pumps may be avoided for injection due to the variable injection pressures that may be experienced. It is understood that the exact procedures utilized in the field will, of course, vary based upon the equipment staged onsite, unique site conditions, and project design.

Site No. 1 Treatment Example 1

Figure 17:
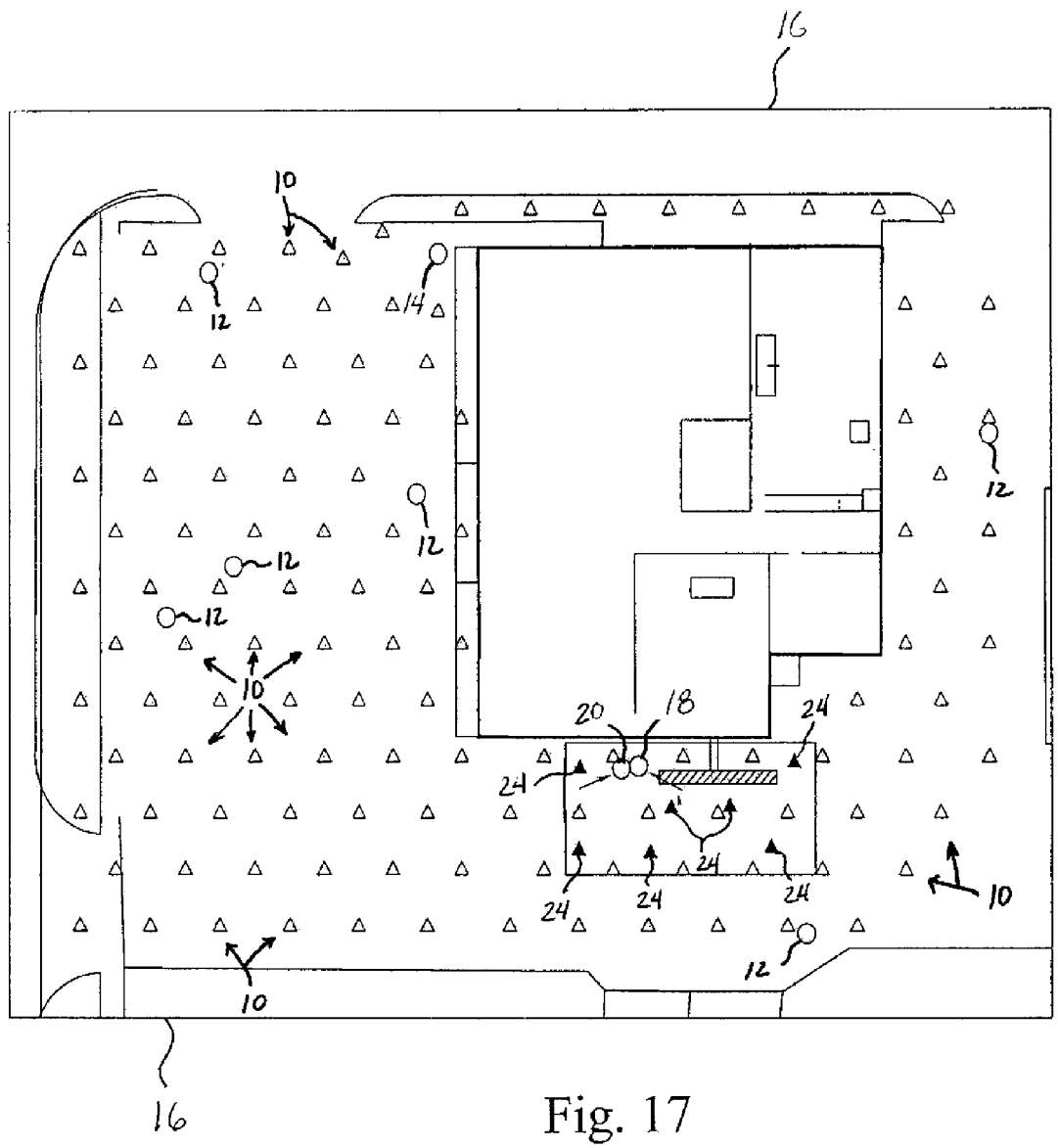
FIG. 17 shows the layout of Site No. 1.

The treatment zone is from 3-9 m below grade. The site is approximately 58 m×40 m in area (FIG. 17). Prior to treatment, tetrachloroethene (PCE) concentrations ranged as high as 3.6 mg/L, trichloroethene (TCE) and cis-1,2-dichloroethene (cis-DCE) ranged as high as 1.3 mg/L, but vinyl chloride (VC) was not detected. A source area was first addressed by permanganate chemical oxidation, followed by injection of 8,864 kg of CAP18 for the full onsite plume area in November 2004. (FIG. 17, open triangles 10 are injection points, and open circles 12 are monitoring wells). Vinyl chloride and ethene were first detected in March 2005, along with reduced groundwater conditions. By December 2006, PCE and TCE in the source area were very near or below cleanup standards; peak concentrations of cis-DCE (12 mg/L), VC (5.8 mg/L) and ethene (3.6 mg/L) occurred in the source area between May and September 2006. One well (14) located downgradient of the source, which was not accessible for treatment in November 2004, yielded increased PCE, no increases in daughter products, and no evidence of anaerobic conditions. The source areas, along with an offsite area not treated in 2004, were addressed by injection of 8,682 kg of CAP18-ME in July 2006. Concentrations in downgradient plume areas remain above cleanup goals, but degradation is evident. The average concentration of PCE has decreased by 81% and the average concentration of TCE has decreased by 89%. Concentrations of cis-DCE, VC, and ethene were at or near historic maxima in December 2006, indicating that the plume remedy is functioning as designed.

Site No. 1 Treatment Example 2

Figure 18:
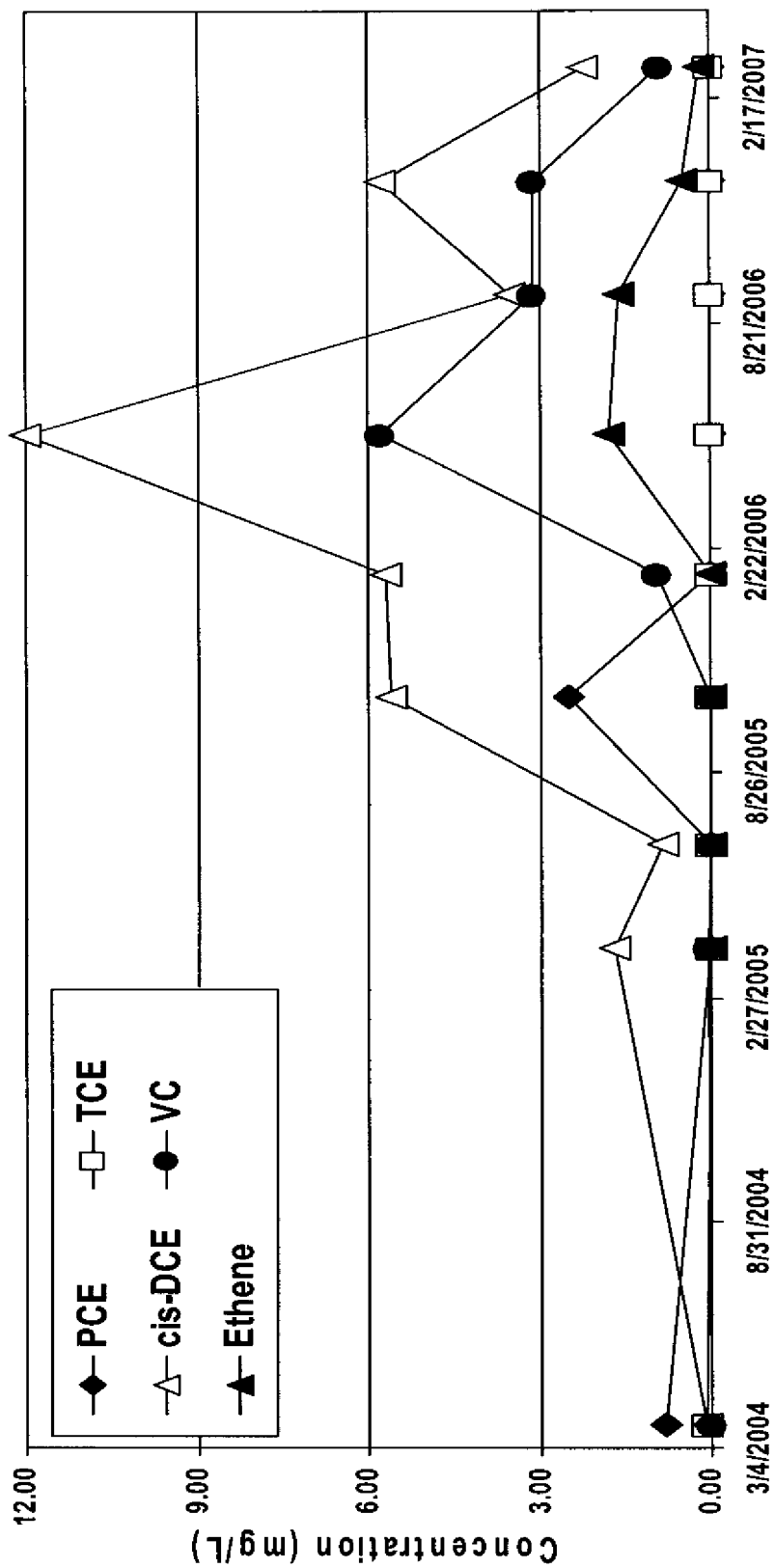
FIG. 18 shows the volatile organic compound (VOC) results from Site No. 1 at Monitoring Well 18.

Approximately 441 kg of 5% sodium permanganate solution was injected into each of seven direct push borings in the primary source area (defined by a rectangle 16 shown on FIG. 17). A concern is that manganese dioxide from the permanganate would inhibit strongly reducing conditions, and corresponding VOC degradation, in the source area. Manganese is reduced from $Mn(VII)$ to $Mn(IV)$ during reduction of permanganate, and the $Mn(IV)$ precipitates as $MnO_2$. However, the $Mn(IV)$ could be further reduced by manganese-reducing bacteria to soluble $Mn(II)$ under reducing conditions, thus effectively acting as a hydrogen sink. Reducing conditions were readily established in monitoring wells 18 and 20, located inside the permanganate injection area (rectangle 16 where solid triangles 24 are permanganate injection points), based upon increased methane concentrations coupled with formation of VC and ethene from biodegradation of PCE and TCE, as shown in FIG. 18. Thus the manganese charge from the permanganate did not appear to inhibit strongly anaerobic conditions from being established in the source area, nor did it appear to generate a significant additional hydrogen demand.

Site No. 2 Treatment Example

Figure 19:
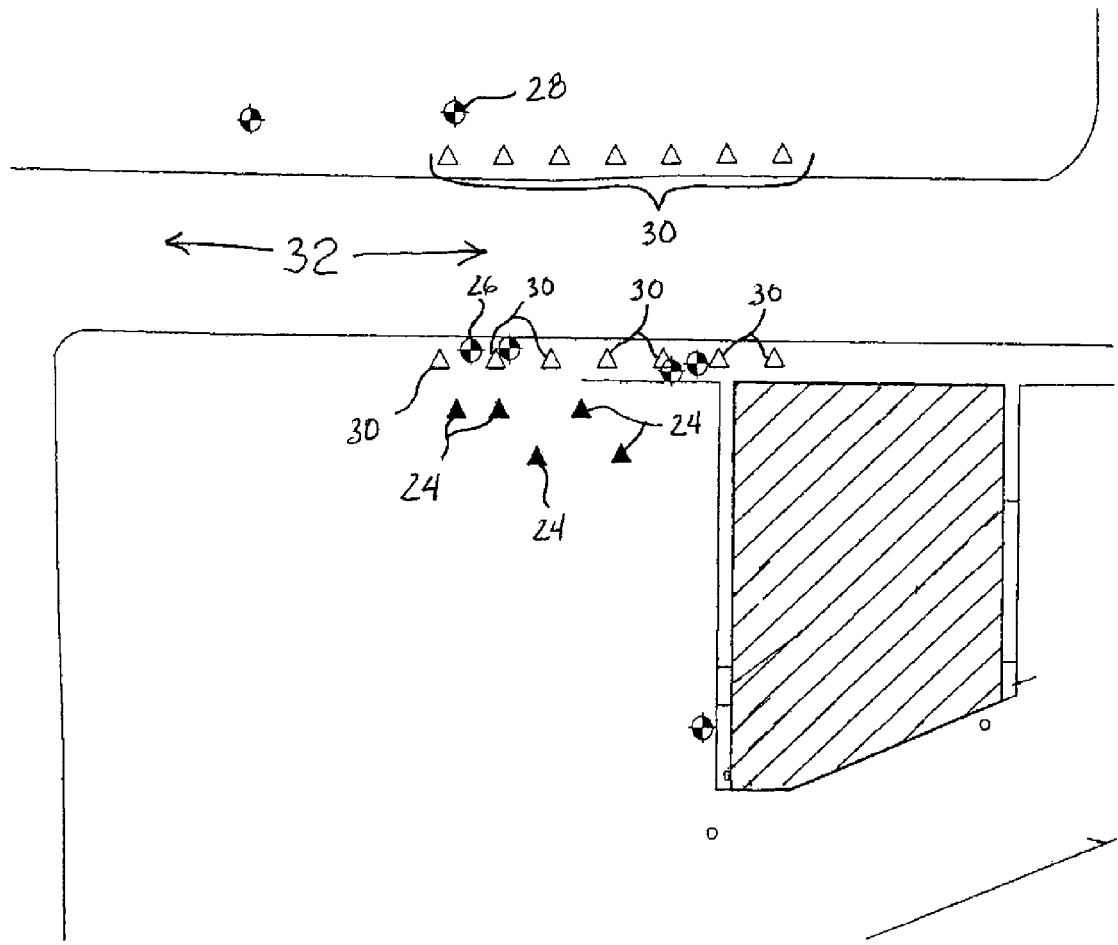
FIG. 19 shows the layout of Site No. 2.

As shown in FIG. 19, the treatment zone is from 4.6-9.1 m below grade. The VOC concentrations are generally low, with maximum onsite concentrations of 0.1 mg/L PCE and 0.099 mg/L cis-DCE. Concentrations within the treatment area (26 and 28) are lower. The design objective was to construct a treatment barrier to address the groundwater plume before it migrated offsite. Approximately 3,773 kg of CAP18 were injected in 14 points (open triangles 30) arranged in two 21-m long barriers on each side of a public street 32 in November 2004, and monitoring wells (26 and 28 were utilized as monitoring locations. (26 initially exhibited decreased TCE concentration (to 0.07 mg/L from 0.1 mg/L) and increasing but low concentrations of cis-1,2-DCE (from not detectable (ND) to 0.018 mg/L), while 28 exhibited a variable TCE concentration. The first detections of cis-DCE were not observed until approximately 11 months after injection. Since that time, TCE concentrations stabilized in 26 and cis-DCE dropped to non-detectable, and in 28 the TCE remained variable while cis-DCE remained elevated.

Figure 20:
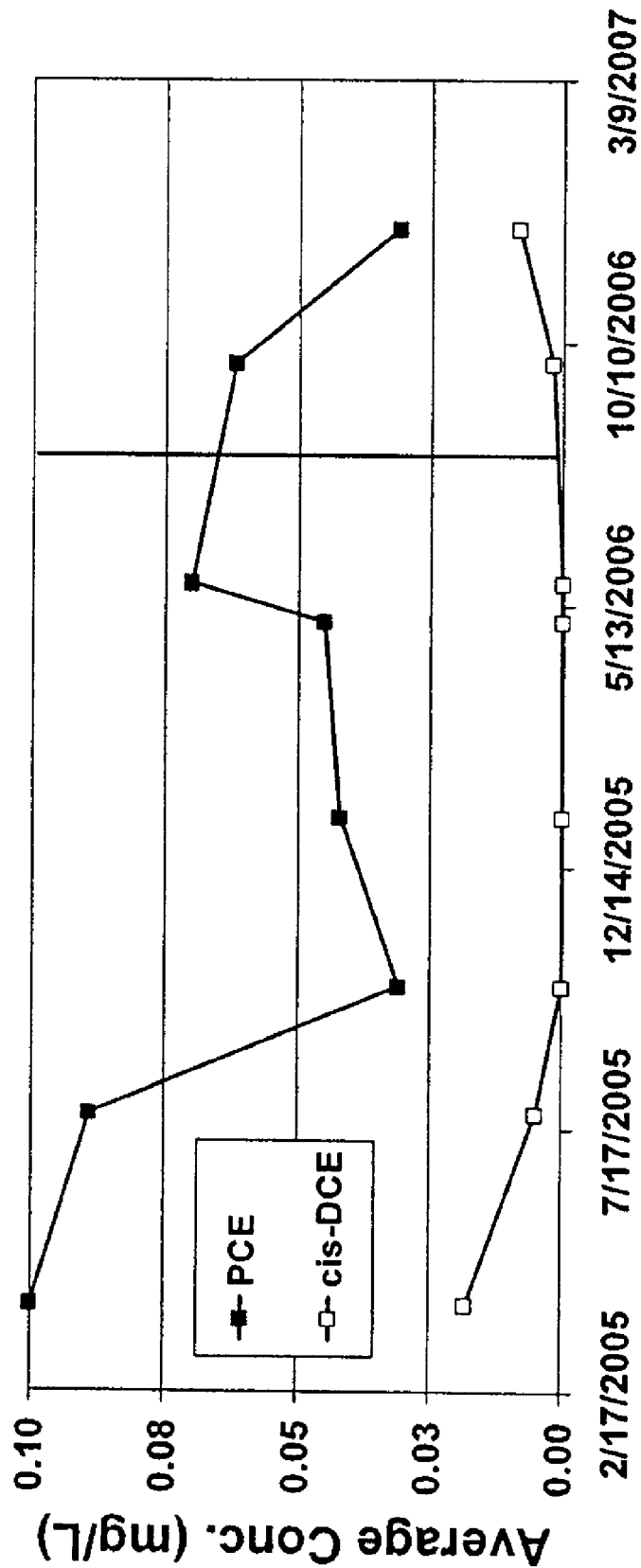
FIG. 20 shows the VOC results from Site No. 2 at Monitoring Well 26. The Site was initially treated with CAP18, then subsequently treated (vertical line) with CAP18-ME.

These results may indicate that either the injection point density in the barriers was insufficient to address the plume, or that the hydrolysis of CAP18 to a more active material capable of supporting microbial metabolism and to stimulate reductive chlorination was insufficiently rapid. In September 2006, 193 kg of CAP18-ME was injected via five direct push injection points (solid triangles 24) located upgradient of 26 (See, FIG. 19). Following that amendment, PCE in 26 has decreased to 0.031 mg/L from 0.070 mg/L, and cis-1,2-DCE has increased to 0.0083 mg/L from undetectable amounts (<0.001 mg/L), as shown in FIG. 20, where the vertical line indicates the time of injection of CAP18-ME. TCE remained undetectable. These data indicate that CAP18-ME provides a more rapid onset of strongly anaerobic conditions to promote bioremediation, and are consistent with laboratory microcosm studies that show CAP18-ME having about a 50% increased rate of TCE degradation than was observed for CAP18. In addition, field pilot application has shown that CAP18-ME accelerated the degradation of PCE compared to CAP18 in a biobarrier application.

The results shown in FIG. 20 also support the observation that CAP18-ME may result in more rapid VOC degradation. Based on the low detection of cis-1,2-DCE, it is likely that the VC and ethene daughter degradation products are being formed at concentrations below the limits of the detection methods. It is understood that these results also indicate that hang-up is not occurring.

Site No. 3 Treatment Example

Figure 21:
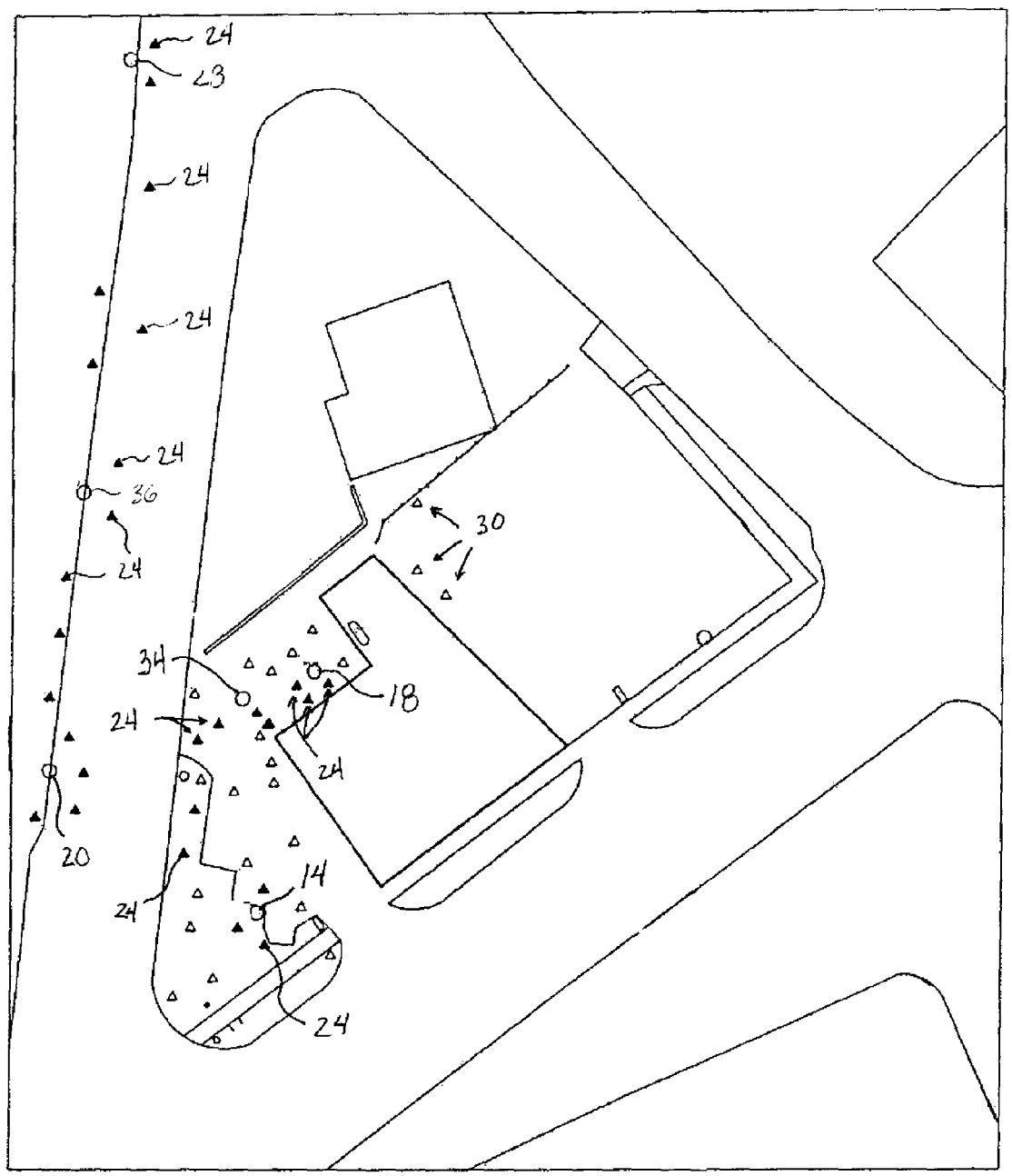
FIG. 21 shows the layout of Site No. 3.

Shallow groundwater at the site is impacted with up to 36,000 µg/L tetrachloroethene (PCE) and its natural degradation product trichloroethene (TCE). Cis-1,2-dichloroethene (cis-DCE) was rarely detected, and vinyl chloride was not detected. TCE and cis-DCE up to 63 µg/L. As shown in FIG. 21, the treatment zone ranged from the water table at 3 m below grade to 9.3 m below grade. PCE concentrations ranged from 8.1 to 36 mg/L in the central portion of the source area (34, 18). Maximum concentrations of breakdown products were 0.26 mg/L TCE, 5.2 mg/L cis-DCE, and 0.68 mg/L VC. Ethene was not analyzed prior to the injection, but was non-detectable in the initial post-injection sampling events.

Figure 22A:
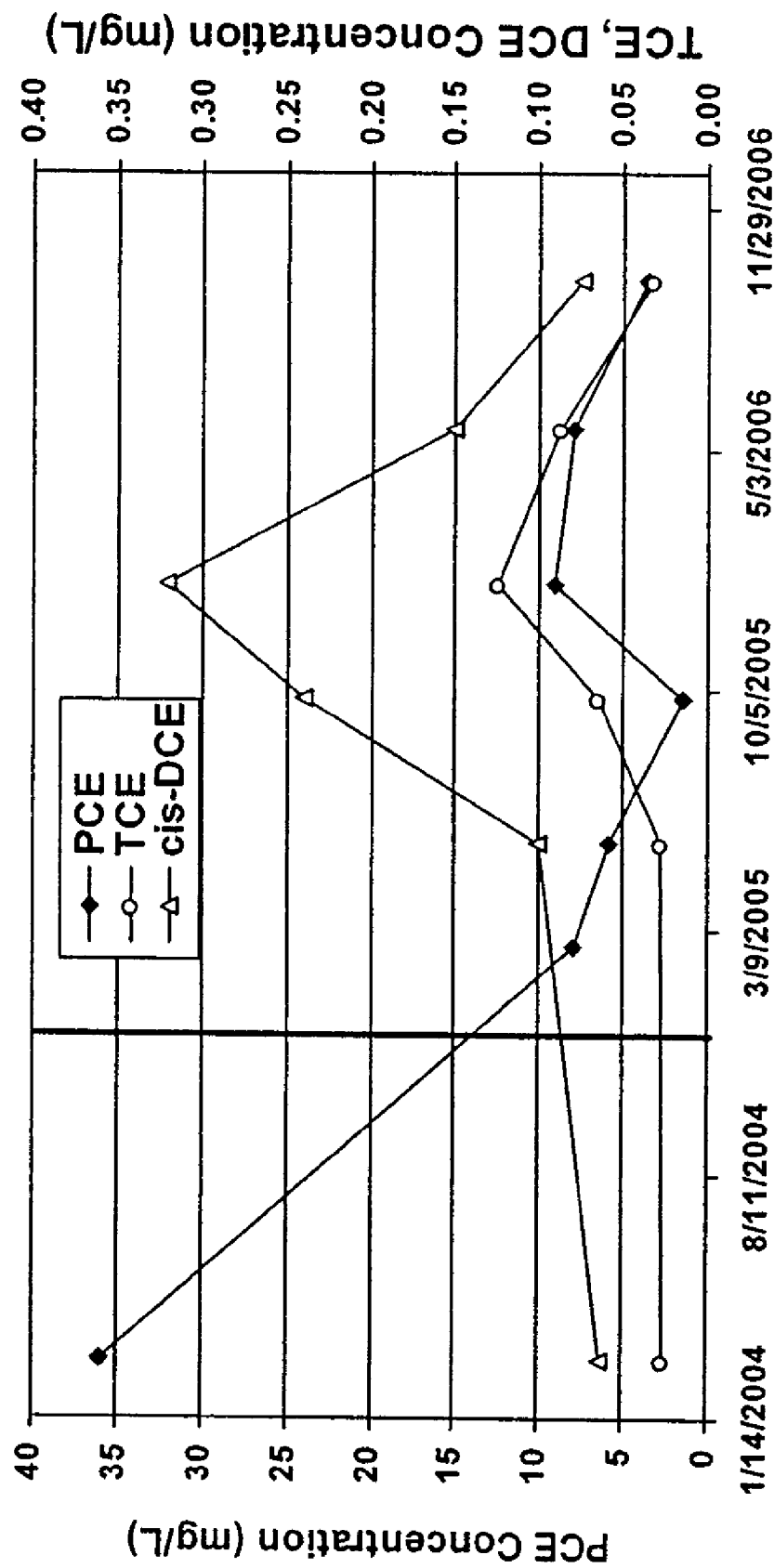
FIGS. 22(a) and 22(b) show the VOC results from Site No. 3 at Monitoring Wells 34 and 18, respectively.
Figure 22B:
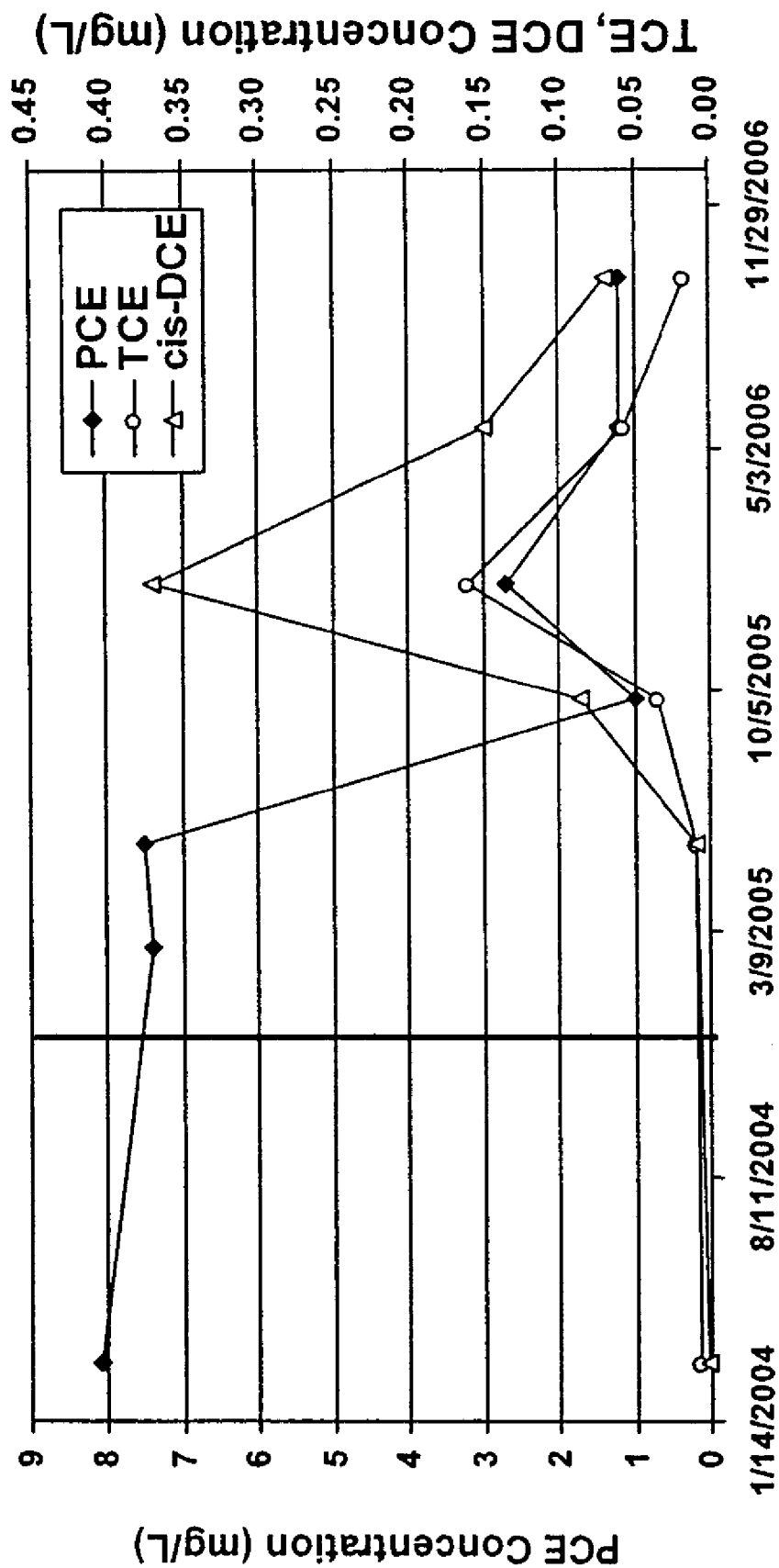

Approximately 1,545 kg of CAP18 were injected via 22 direct-push points injection points (open triangles 30) in November 2004; each point received 154 lbs (20 gallons) of CAP18. By September 2006, PCE concentrations in the source area wells (34 and 18) decreased by 85-90%, but with relatively low associated increases in TCE and cis-1,2-DCE concentrations and no increase in VC or ethene. 14 exhibited little evidence of treatment, but was not located near the injection points. In October 2006, an additional 1,897 kg of CAP18-ME were injected via 27 injection points (solid triangles 24); each point received approximately 154 lbs (20 gallons) of CAP18-ME. The supplementary injection augmented the source area near monitoring wells 14, 34, and 18, and also established a barrier wall along the downgradient margin of the site. 34 has exhibited a 90% reduction in PCE concentration (to 3.6 mg/L from 36 mg/L) and 18 has exhibited an 85% reduction in PCE concentration. TCE and cis-DCE concentrations have reached peaks and continue to decline. Neither well has yet exhibited the formation of vinyl chloride or ethene, which is expected. However, because the cis-DCE concentrations have declined over the last two sampling events, hang-up (lack of degradation) of cis-DCE is not occurring. The results for the change in PCE concentration at Site 3 as indicated at Monitoring Wells 34 and 18 are shown in FIGS. 22(a) and 22(b), respectively, where the vertical line indicates the time of injection of CAP18-ME.

The large decreases in PCE observed in 34 and 18, without associated increases in daughter product concentrations, indicate that partitioning of VOCs into the CAP18 may be an important mechanism for VOC loss from groundwater at this site. Additional data for other wells in the CAP18-ME treatment area are shown in the following Table (where NS indicates not sampled).

Site 3 Groundwater Data (Concentrations in mg/L)

| | Location/Date | PCE | TCE | cis-DCE | VC | Ethene | Ethane | Methane | Sulfate | TOC |
|---|---|---|---|---|---|---|---|---|---|---|
| 14 | Dec. 20, 2006 | 0.37 | 0.0019 | 0.0036 | <0.001 | <0.01 | <0.0092 | 0.93 | NS | NS |
| | Sep. 27, 2006 | 0.33 | <0.001 | 0.0033 | <0.001 | <0.1 | <0.1 | 1.6 | NS | NS |
| | May 22, 2006 | 0.48 | <0.005 | <0.005 | <0.01 | 0.000059 | <0.000025 | 1.7 | NS | NS |
| | Jan. 6, 2006 | 0.22 | <0.001 | <0.001 | <0.001 | <0.01 | <0.01 | <0.01 | 66 | 2 |
| | Sep. 29, 2005 | 0.17 | <0.001 | <0.001 | <0.001 | <0.01 | <0.01 | <0.01 | NS | NS |
| | May 26, 2005 | 0.18 | <0.001 | <0.001 | <0.001 | <0.01 | <0.01 | <0.01 | 100 | 1 |
| | Feb. 24, 2005 | 0.2 | <0.001 | <0.001 | <0.001 | <0.01 | <0.01 | <0.01 | 93 | NS |
| | Mar. 4, 2004 | 0.14 | <0.005 | <0.005 | <0.005 | NS | NS | NS | NS | NS |
| 34 | Dec. 20, 2006 | 4.0 | 0.019 | 0.052 | <0.001 | <0.01 | <0.0092 | 0.38 | NS | NS |
| | Sep. 27, 2006 | 3.6 | 0.033 | 0.074 | <0.01 | <0.1 | <0.1 | 0.13 | NS | NS |
| | May 22, 2006 | 8.0 | 0.087 | 0.15 | <0.01 | <0.000025 | <0.000025 | 0.0094 | NS | NS |
| | Jan. 5, 2006 | 9.0 | <0.25 | 0.32 | <0.25 | <0.01 | <0.01 | <0.01 | 53 | NS |
| | Sep. 28, 2005 | 1.4 | 0.065 | 0.24 | <0.02 | <0.01 | <0.01 | <0.01 | NS | NS |
| | May 26, 2005 | 5.8 | 0.028 | 0.1 | <0.02 | <0.01 | <0.01 | <0.001 | 63 | 1.2 |
| | Feb. 24, 2005 | 8 | <0.5 | <0.5 | <0.5 | <0.01 | <0.01 | <0.01 | 83 | NS |
| | Mar. 4, 2004 | 36 | 0.026 | 0.063 | <0.005 | NS | NS | NS | NS | NS |
| 18 | Dec. 21, 2006 | 0.78 | 0.012 | 0.083 | <0.001 | <0.01 | <0.0092 | 0.28 | NS | NS |
| | Sep. 27, 2006 | 1.2 | 0.016 | 0.07 | <0.001 | <0.01 | <0.01 | 0.45 | NS | NS |
| | May 22, 2006 | 1.2 | 0.056 | 0.15 | <0.01 | <0.000025 | <0.000025 | 0.026 | NS | NS |
| | Jan. 5, 2006 | 2.7 | 0.16 | 0.370 | <0.02 | <0.01 | <0.01 | 0.13 | 38 | 2.1 |
| | Sep. 29, 2005 | 1.0 | 0.034 | 0.085 | <0.02 | <0.01 | <0.01 | 0.02 | NS | NS |

-continued

| | Location/Date | PCE | TCE | cis-DCE | VC | Ethene | Ethane | Methane | Sulfate | TOC |
|---|---|---|---|---|---|---|---|---|---|---|
| | May 26, 2005 | 7.5 | <0.02 | <0.02 | <0.02 | <0.01 | <0.01 | <0.01 | 65 | 1.9 |
| | Feb. 25, 2005 | 7.4 | <0.5 | <0.5 | <0.5 | <0.01 | <0.01 | <0.01 | 60 | NS |
| | Mar. 5, 2004 | 8.1 | 0.007 | <0.005 | <0.005 | NS | NS | NS | NS | NS |
| 20 | Dec. 20, 2006 | 0.21 | 0.0076 | 0.016 | 0.00076 | <0.01 | <0.0092 | <0.00037 | NS | NS |
| | Sep. 27, 2006 | 0.032 | 0.0028 | 0.014 | <0.001 | <0.01 | <0.01 | <0.01 | NS | NS |
| | May 22, 2006 | 0.820 | 0.088 | 0.19 | <0.01 | <0.000025 | 0.00025 | 0.0019 | NS | NS |
| | Jan. 7, 2006 | 0.76 | 0.089 | 0.22 | 0.0049 | <0.01 | <0.01 | <0.01 | 70 | 2.0 |
| | Sep. 29, 2005 | 0.62 | 0.078 | 0.09 | 0.0018 | <0.01 | <0.01 | <0.01 | NS | NS |
| | Mar. 5, 2004 | 0.36 | 0.0067 | 0.0088 | <0.005 | NS | NS | NS | NS | NS |
| 36 | Dec. 20, 2006 | 0.019 | <0.0026 | 3.1 | 0.83 | 0.034 | <0.00092 | 3.6 | NS | NS |
| | Sep. 27, 2006 | 0.140 | <0.1 | 4.0 | 0.98 | <.1 | <.1 | 160 | NS | NS |
| | May 23, 2006 | 0.023 | <0.005 | 3.3 | 1.1 | 0.069 | 0.0056 | 3.4 | NS | NS |
| | Jan. 6, 2006 | <.10 | <.10 | 5.4 | 0.91 | <0.01 | <0.01 | 2.3 | <5.0 | 3.8 |
| | Sep. 29, 2005 | <0.5 | <0.5 | 5.6 | <0.5 | 0.02 | <0.01 | 0.9 | NS | NS |
| | Jun. 23, 2005 | <0.05 | <0.05 | 3.6 | 0.83 | <0.1 | <0.1 | 2.3 | <5.0 | 3.0 |
| | Feb. 25, 2005 | 0.14 | <0.05 | 3.1 | 0.62 | <0.1 | <0.1 | 2.9 | 9.6 | NS |
| | Mar. 5, 2004 | 0.13 | 0.11 | 5.2 | 0.68 | NS | NS | NS | NS | NS |
| 28 | Dec. 21, 2006 | 0.00045 | 0.00039 | 0.014 | 0.0085 | <.001 | <.00092 | <0.00037 | NS | NS |
| | Sep. 27, 2006 | <0.001 | <0.001 | 0.011 | 0.02 | <.01 | <.01 | 0.25 | NS | NS |
| | May 23, 2006 | 0.067 | <0.005 | 0.074 | 0.048 | 0.013 | 0.0012 | 0.7 | NS | NS |
| | Jan. 6, 2006 | <0.001 | <0.001 | 0.022 | 0.030 | NS | NS | NS | NS | NS |
| | Sep. 29, 2005 | <0.001 | <0.001 | 0.032 | 0.012 | <0.01 | <0.01 | 0.19 | NS | NS |
| | Jun. 23, 2005 | <0.001 | <0.001 | 0.039 | 0.011 | <0.01 | <0.01 | 0.44 | 26 | 5.7 |
| | Feb. 25, 2005 | 0.009 | <0.001 | 0.02 | 0.0048 | <0.01 | <0.01 | 0.34 | 29 | NS |
| | Mar. 5, 2004 | <0.005 | <0.005 | 0.0074 | 0.0026 | NS | NS | NS | NS | NS |

What is claimed is:

1. A composition comprising a methyl ester of a fatty acid and a bioremediation reagent, where the bioremediation reagent is an acyl glycerol, and where said composition is capable of supporting the growth of a microbial population in the presence of an electron acceptor.

2. The composition of claim 1 wherein the methyl ester of the fatty acid is an oil derivative.

3. The composition of claim 2 wherein the oil is a vegetable oil.

4. The composition of claim 1 wherein the methyl ester of the fatty acid comprises $C_{18}$ fatty acid esters.

5. The composition of claim 1 wherein the methyl ester of the fatty acid comprises at least about a 50% $C_{18}$ fatty acid ester fraction.

6. The composition of claim 1 wherein the methyl ester of the fatty acid comprises at least about an 80% $C_{18}$ fatty acid ester fraction.

7. The composition of claim 1 wherein the methyl ester of the fatty acid comprises no more than about a 25% saturated fatty acid ester fraction.

8. The composition of claim 1 wherein the methyl ester of the fatty acid comprises no more than about a 15% saturated fatty acid ester fraction.

9. The composition of claim 1 wherein the acyl glycerol is a vegetable oil or a derivative of a vegetable oil.

10. The composition of claim 1 wherein the bioremediation reagent comprises at least about a 50% $C_{18}$ fatty acid fraction.

11. The composition of claim 1 wherein the bioremediation reagent comprises at least about an 80% $C_{18}$ fatty acid fraction.

12. The composition of claim 1 wherein the bioremediation reagent comprises no more than about a 25% saturated fatty acid fraction.

13. The composition of claim 1 wherein the bioremediation reagent comprises no more than about a 15% saturated fatty acid fraction.

14. The composition of claim 1 wherein the methyl ester of the fatty acid is a derivative of a first vegetable oil and the bioremediation reagent is a second vegetable oil or a derivative of a second vegetable oil.

15. The composition of claim 14 wherein the first and second vegetable oils are different.

16. The composition of claim 14 wherein the first and second vegetable oils are the same.

17. The composition of claim 1 wherein at least one of the methyl ester, the bioremediation reagent, or the composition is emulsified.

18. The composition of claim 1 adapted for administration to a site comprising a contamination.

19. The composition of claim 18 where the site is subsurface.

20. The composition of claim 18 where the site is a subsurface groundwater site.

21. The composition of claim 1 wherein the microbial population is present in an aquifer or vadose zone and the composition is capable of supporting the growth of the microbial population.

22. The composition of claim 1 wherein the ratio of the methyl ester of the fatty acid to the bioremediation reagent is in the range from about 1:99 to about 25:75.

23. The composition of claim 1 wherein the ratio of the methyl ester of the fatty acid to the bioremediation reagent is in the range from about 5:95 to about 15:85.

24. A method for in situ remediation of a contamination in an aquifer or vadose zone, the method comprising the step of contacting the composition of claim 1 with the contamination in the aquifer or vadose zone in an amount effective to sustain a population of anaerobic bacteria in the aquifer or vadose zone.

25. The method of claim 24 wherein the contamination comprises an organic solvent.

26. The method of claim 24 wherein the contamination comprises a chlorinated organic solvent.

27. The method of claim 24 wherein the contamination comprises an inorganic nitrogen or inorganic sulfur compound.

28. The method of claim 24 wherein the contamination comprises an organic nitrogen compound.

29. The method of claim 24 wherein the population of anaerobic bacteria is naturally occurring in the aquifer or vadose zone.

30. The method of claim 24 further comprising the step of introducing a population of anaerobic bacteria in the aquifer or vadose zone.

\* \* \* \* \*